United States Patent [19]

Yoshimura et al.

[11] Patent Number: 5,237,091

[45] Date of Patent: Aug. 17, 1993

[54] NAPHTHALENE DERIVATIVES

[75] Inventors: Hiroyuki Yoshimura; Shinya Abe; Tetsuya Kawahara; Naoyuki Shimomura; Kazuo Okano; Richard S. J. Clark; Takashi Mori; Shuhei Miyazawa; Ryoichi Hashida; Kenzo Muramoto; Koukichi Harada; Takashi Inoue, all of Ibaraki, Japan; Hiroshi Shirota, Evanston, Ill.; Kenichi Chiba, Ibaraki, Japan; Kenichi Kusube, Ibaraki, Japan; Toru Horie, Ibaraki, Japan; Takeshi Suzuki, Ibaraki, Japan; Isao Yamatsu, Ibaraki, Japan

[73] Assignee: Eisai Co., Ltd., Tokyo, Japan

[21] Appl. No.: 890,223

[22] Filed: May 29, 1992

Related U.S. Application Data

[62] Division of Ser. No. 790,541, Nov. 12, 1991.

[30] Foreign Application Priority Data

Nov. 16, 1990 [JP] Japan ................................ 2-311066

[51] Int. Cl.$^5$ ............................................ C07C 69/76

[52] U.S. Cl. ..................................... 560/53; 562/462; 568/328; 568/633

[58] Field of Search ........................ 560/53; 562/462; 568/328, 33

[56] References Cited

PUBLICATIONS

J. Libman Tetrahedron Letters No. 29 pp. 2507–2510 1975.

Chemical Abstracts, vol. 113, No. 5, Jul. 1990 No. 40087 Rearrangements of Nonidolizable arylhydroazones etc p. 560 col. 2.

Chemical Abstracts, vol. 112, No. 19, May 1990 Abstract No. 178286 Convenient Route to 1,2-dibenzoyl-1-Arylethylenes p. 698, col. 2.

Chemical Abstracts, vol. 75, No. 25, Dec. 1971 Abstract No. 151608 "Stable O-and P-Naphtoquinone Methides" p. 307, col. 1.

Primary Examiner—Paul J. Killos
Attorney, Agent, or Firm—Nixon & Vanderhye

[57] ABSTRACT

The present invention relates to a naphthalene derivative. More particularly, it relates to a naphthalene derivative exhibiting an excellent activity as a drug.

5 Claims, No Drawings

NAPHTHALENE DERIVATIVES

This is a division of U.S. application Ser. No. 07/790,541, filed Nov. 12, 1991.

BACKGROUND OF THE INVENTION AND PRIOR ARTS

Although various nonsteroidal anti-inflammatory drugs have already been put on the market, they are all unsatisfactory in respect of efficacy, so that the development of an anti-inflammatory drug from new standpoints has been eagerly expected.

It has already been known that the inhibition of production of prostaglandins (PGs) brings about an anti-inflammatory effect. Meanwhile, many studies have recently been made on leukotrienes (LTs) to make their physiological activities apparent. That is, $LTB_4$ exhibits an activity of highly activating the migration of leukocyte to cause the excess accumulation thereof, thus contributing to the acceleration of inflammatory reactions, while $LTC_4$ and $D_4$ have been ascertained to exhibit an effect of enhancing the permeability of a blood vessel. Accordingly, it is conceivable that a more excellent anti-inflammatory drug can be developed if the inhibitory activity against LTs production is combined with that against PGs production at a well-balanced activity ratio. Further, such an anti-inflammatory drug may be effectively applied to asthma, inflammatory dermatitis, inflammatory enteric diseases, arthritis and so on by virtue of its pathological effects.

No drug has been developed as yet from the standpoint described above.

Under these circumstances, the inventors of the present invention have eagerly studied for many years and have found that a naphthalene derivative which will be described below acts as an excellent anti-inflammatory drug. The present invention has been accomplished on the basis of this finding.

With respect to naphthalene derivatives, for example, Japanese Patent Laid-Open No. 263943/1986 discloses naphthalene derivatives exhibiting an inhibitory activity against 5-lipoxygenase, while Aust. J. Chem., 30, 2241 (1977) discloses those substituted with an alkenylcarboxylic acid group at the 1-position. However, not only these derivatives are distinguishable from those of the present invention in respect of chemical structure, but also these documents are silent on the efficacy thereof as a drug.

SUMMARY OF THE INVENTION

The compound of the present invention is a naphthalene derivative represented by the following general formula (I) or a pharmacologically acceptable salt thereof:

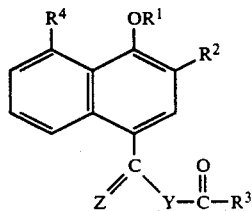

wherein $R^1$ stands for a hydrogen atom or a lower alkyl, acyl or arylalkyl group;

$R^2$ stands for a hydrogen atom or a lower alkyl, lower alkoxy, cycloalkoxy or acyl group;

$R^3$ stands for a hydroxyl group, a group capable of forming an ester together the carboxyl group represented by the formula:

wherein $R^3$ is a hydroxyl group, or a group represented by the formula:

(wherein $R^{10}$ and $R^{11}$ may be the same or different from each other and each stands for a hydrogen atom, a hydroxyl, lower alkyl, lower alkoxy, aryl, heteroaryl group or a group represented by the formula: $—(CH_2)_q—COOH$ (wherein q is an integer of 1 to 2), or alternatively $R^{10}$ and $R^{11}$ may form a ring which may contain a nitrogen, oxygen or sulfur atom together with the nitrogen atom to which $R^{10}$ and $R^{11}$ are bonded);

Z stands for a group represented by the formula:

(wherein $R^5$ and $R^6$ may be the same or different from each other and each stands for a hydrogen atom or a lower alkyl, alkenylalkyl, alkynylalkyl or aryl group, an arylalkyl group, the aryl group of which may be substituted, a halogen atom or a heteroarylalkyl, cycloalkyl, cycloalkylalkyl, lower alkoxyalkyl, heterocycloalkyl or cyano group, or alternatively $R^5$ and $R^6$ may form a ring together with the carbon atom to which $R^5$ and $R^6$ are bonded), a group represented by the formula: $=N\text{-}OR^7$ (wherein $R^7$ stands for a lower alkyl group) or an oxygen atom;

Y stands for a group represented by the formula: $—(CH_2)n—$ (wherein n is 0 or integer of 1 to 2) or a group represented by the formula:

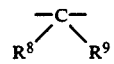

(wherein $R^8$ and $R^9$ may be the same or different from each other and each stands for a lower alkyl group); and $R^4$ stands for a hydrogen atom, a lower alkyl group or a group represented by the formula:

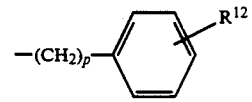

(wherein p is 0 or an integer of 1 to 3 and $R^{12}$ stands for a hydrogen or halogen atom or a lower alkyl or lower alkoxy group).

Among these naphtahlene derivatives as defined the general formula (I) or pharmacologically acceptable salts thereof, a compound that R⁴ in the general formula (I) is a benzyl group is preferable.

Among these naphtahlene derivatives as defined the general formula (I) or pharmacologically acceptable salts thereof, a compound that R¹ in the general formula (I) is a hydrogen atom or a lower alkyl group is preferable, and a compound that R¹ in the general formula (I) is a methyl group is more preferable.

Among these naphtahlene derivatives as defined the general formula (I) or pharmacologically acceptable salts thereof, a compound that R² in the general formula (I) is a lower alkoxyl group is preferable, and a compound that R² in the general formula (I) is a methoxyl group is more preferable.

Among these naphtahlene derivatives as defined the general formula (I) or pharmacologically acceptable salts thereof, a compound that R³ in the general formula (I) is a hydroxyl group is preferable.

Among these naphtahlene derivatives as defined the general formula (I) or pharmacologically acceptable salts thereof, a compound that Y in the general formula (I) is a group represented by the formula: $-(CH_2)_n-$ (wherein n is 0) is preferable.

Among these naphtahlene derivatives as defined the general formula (I) or pharmacologically acceptable salts thereof, a compound that Z in the general formula (I) is a group represented by the formula:

(wherein R⁵ and R⁶ may be the same or different from each other and each stands for a hydrogen atom, a lower alkyl group, an alkenylalkyl group, an arylalkyl group whose aryl group may be substituted or a halogen atom) is preferable.

Among these naphtahlene derivatives as defined the general formula (I) or pharmacologically acceptable salts thereof, a compound that in the general formula (I), R¹ is a hydrogen atom, R² is a methoxy group, R³ is a hydroxyl group, Y is a group represented by the formula: $-(CH_2)_n-$ (wherein n is 0), Z is a group represented by the formula:

(wherein R⁵ and R⁶ may be the same or different from each other and each stands for a hydrogen atom, a lower alkyl group, an alkenylalkyl group, an arylalkyl group whose aryl group may be substituted or a halogen atom), and R⁴ is a benzyl group is preferable.

Among these naphtahlene derivatives as defined the general formula (I) or pharmacologically acceptable salts thereof, a compound selected from the group consisting of the below listed naphtahlene derivatives is preferable.

(Z)-2-(5-benzyl-4-hydroxy-3-methoxy-1-naphtyl)-2-butenoic acid;
(Z)-2-(5-benzyl-4-hydroxy-3-methoxy-1-naphtyl)-2-pentenoic acid;
(Z)-2-(5-benzyl-4-hydroxy-3-methoxy-1-naphtyl)-2-hexenoic acid;
(Z)-2-(5-benzyl-4-hydroxy-3-methoxy-1-naphtyl)-4-methoxy-2-pentenoic acid;
(Z)-2-(5-benzyl-4-hydroxy-3-methoxy-1-naphtyl)-2,5-hexadienoic acid;
(Z)-2-(5-benzyl-4-hydroxy-3-methoxy-1-naphtyl)-2-heptenoic acid;
(Z)-2-(5-benzyl-4-hydroxy-3-methoxy-1-naphtyl)-3-propenoic acid;
(Z)-2-(5-benzyl-4-hydroxy-3-methoxy-1-naphtyl)-4-phenyl-2-butenoic acid;
(Z)-2-(5-benzyl-4-hydroxy-3-methoxy-1-naphtyl)-3-cyclohexyl-2-propenoic acid;
(Z)-2-(5-benzyl-4-hydroxy-3-methoxy-1-naphtyl)-4,4-dimethyl-2-pentenoic acid;
2-(5-Benzyl-4-hydroxy-3-methoxy-1-naphtyl)-2-propenoic acid;
2-(5-Benzyl-4-hydroxy-3-methoxy-1-naphtyl)-2-butenoic acid;
(E)-2-(5-benzyl-4-hydroxy-3-methoxy-1-naphtyl)-2-butenoic acid;
2-(5-Benzyl-4-hydroxy-3-methoxy-1-naphtyl)-3,3-dichloro-2-propenoic acid;
(Z)-2-(5-benzyl-4-hydroxy-3-methyl-1-naphtyl)-2-butenoic acid;
2-(5-Benzyl-4-hydroxy-3-methyl-1-naphtyl)-3-methyl-2-butenoic acid;
(E)-2-(5-benzyl-4-hydroxy-3-methoxy-1-naphtyl)-2-pentenoic acid;
(E)-2-(5-benzyl-4-hydroxy-3-methoxy-1-naphtyl)-2-hexenoic acid;
(Z)-2-(5-benzyl-4-hydroxy-3-ethoxy-1-naphtyl)-2-butenoic acid;
(Z)-2-(5-benzyl-4-acetoxy-3-methoxy-1-naphtyl)-4-methyl-2-pentenoic acid;
(Z)-2-(5-benzyl-4-acetoxy-3-methoxy-1-naphtyl)-2-hexenoic acid;
(E)-2-(5-benzyl-4-acetoxy-3-methoxy-1-naphtyl)-2-butenoic acid;
(Z)-2-(5-benzyl-4-acetoxy-3-methoxy-1-naphtyl)-2-butenoic acid;
(Z)-2-(5-benzyl-4-acetyloxy-3-methoxy-1-naphtyl)-2-pentenoic acid; and
(Z)-2-(5-benzyl-4-hydroxy-3-methoxy-1-naphtyl)-4-methyl-2-pentenoic acid.

A pharmaceutical composition of the present invention comprises a therapeutically effective amount of the above-mentioned naphthalene derivative or the pharmacologically acceptable salt thereof and a pharmacologically acceptable carrier.

A method for treatment of a disease of the present invention comprises administering a pharmaceutically effective amount of the above-mentioned naphthalene derivative or the pharmacologically acceptable salt thereof to a patient suffering from a disease which the production of prostaglandin is rised.

A method for treatment of a disease of the present invention comprises administering a pharmaceutically effective amount of the above-mentioned naphthalene derivative or the pharmacologically acceptable salt thereof to a patient suffering from a disease which the production of leukotrienes is rised.

A method for treatment of a disease of the present invention comprises administering a pharmaceutically effective amount of the above-mentioned naphthalene derivative or the pharmacologically acceptable salt thereof to a patient suffering from an inflammatory disease.

A method for treatment of a disease of the present invention comprises administering a pharmaceutically effective amount of the above-mentioned naphthalene derivative or the pharmacologically acceptable salt thereof to a patient suffering from a disease selected from the group consisting of chronic rheumatoid arthritis, osteoarthritis, shoulder periarthritis, cervicobrachial syndrome and lumbago.

Furthermore, use of the present invention comprises the use of the above-mentioned naphthalene derivative or the pharmacologically acceptable salt thereof for the making of a medicament for treating a disease which the production of prostaglandin is rised.

Use of the present invention comprises the use of the above-mentioned naphthalene derivative or the pharmacologically acceptable salt thereof for the making of a medicament for treating a disease which the production of leukotrienes is rised.

Use of the present invention comprises the use of the above-mentioned naphthalene derivative or the pharmacologically acceptable salt thereof for the making of a medicament for treating an inflammatory disease.

Use of the present invention comprises the use of the above-mentioned naphthalene derivative or the pharmacologically acceptable salt thereof for the making of a medicament for treating a disease selected from the group consisting of chronic rheumatoid arthritis, osteoarthritis, shoulder periarthritis, cervicobrachial syndrome and lumbago.

The intermediate of the present invention is a naphthalene derivative represented by the following general formula (A):

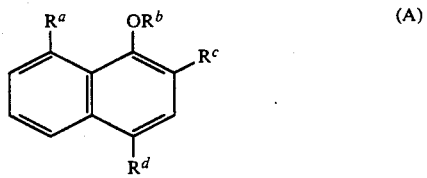

(A)

wherein $R^a$ means a benzyl group, $R^b$ stands for a hydrogen atom or a lower alkyl group, $R^c$ stands for a hydrogen atom or a lower alkyl group and $R^d$ represents a hydrogen atom or a group represented by the formula:

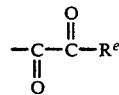

(wherein $R^e$ stands for a hydroxyl group or a lower alkyl group).

Among these intemediates (naphthalene derivatives) as defined the general formula (A), a compound selected from the group consisting of the below listed naphtahlene derivatives is preferable.

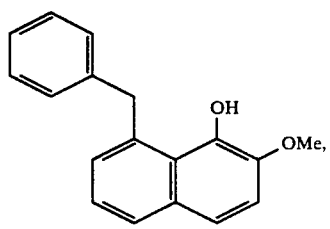

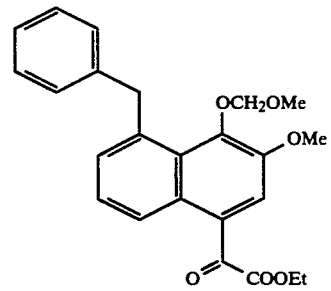

and

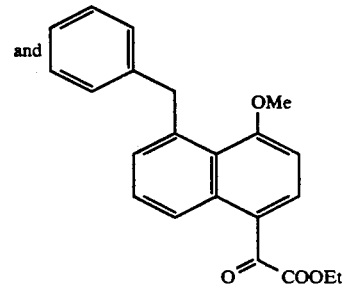

DETAILED DESCRIPTION OF THE INVENTION

In this specification, the position numbers of carbon atoms constituting the naphthalene ring are as follows:

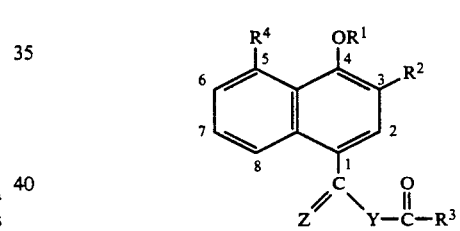

In the above definition of the compound (I) according to the present invention, the lower alkyl group defined with respect to $R^1$, $R^2$, $R^4$, $R^5$, $R^6$, $R^7$, $R^8$, $R^9$, $R^{10}$, $R^{11}$ and $R^{12}$ is a straight-chain or branched alkyl group having 1 to 6 carbon atoms and examples thereof include methyl, ethyl, propyl, isopropyl, butyl, isobutyl, sec-butyl, tert-butyl, pentyl(amyl), isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups. Among these groups, methyl group, ethyl group, propyl group and isopropyl group are desirable.

The lower alkoxy group defined with respect to $R^2$, $R^{10}$, $R^{11}$ and $R^{12}$ is one derived from the above-mentioned lower alkyl group having 1 to 6 carbon atoms and preferable examples thereof include methoxy group, ethoxy group, n-propoxy group, isopropoxy group and n-butoxy group, among which methoxy group is most desirable.

The halogen atom defined with respect to $R^5$, $R^6$ and $R^{12}$ is chlorine, bromine, iodine or fluorine.

The cycloalkyl group defined with respect to $R^5$ and $R^6$ is one having 3 to 7 carbon atoms and examples thereof include cyclopropyl group, cyclobutyl group, cyclopentyl group, cyclohexyl group and cycloheptyl group.

The cycloalkylalkyl group defined with respect to $R^5$ and $R^6$ is one derived from the above-mentioned cycloalkyl group and representative examples thereof include cyclopentylmethyl group, cyclopropylmethyl group, cyclohexylmethyl group and cyclohexylethyl group.

The aryl group defined with respect to $R^2$, $R^5$, $R^6$, $R^{10}$ and $R^{11}$ includes a phenyl group, a naphthyl group and so on which may be substituted with a lower alkyl group such as a methyl group, a ethyl group, a halogen atom and a lower alkoxy group.

The arylalkyl group defined with respect to $R^1$, $R^5$ and $R^6$ is one derived from the above-mentioned aryl group. The most desirable examples thereof include benzyl group and phenethyl group, the aryl group of which may be substituted with a methyl group, a ethyl group or a halogen atom.

The heteroaryl group defined with respect to $R^{10}$ and $R^{11}$ is a heterocyclic group such as a pyridyl group, a furyl group and a pyrimidyl group.

The lower alkoxyalkyl group defined with respect to $R^5$ and $R^6$ is one derived from the above-mentioned lower alkoxy group and examples thereof include methoxyethoxy group, methoxypropoxy group and ethoxyethoxy group.

The acyl group defined with respect to $R^2$ is a residue of an organic acid such as an aliphatic saturated or unsaturated carboxylic acid and a carbocyclic or heterocyclic carboxylic acid and particular examples thereof include lower alkanoyl groups such as formyl group, acetyl group, propionyl group, butyryl group, isobutyryl group, valeryl group, isovaleryl group and pivaloyl group; aroyl groups such as benzoyl group, toluoyl group and naphthoyl group; and heteroaroyl groups such as furoyl group, nicotinoyl group and isonicotinoyl group.

Further, $R^{10}$ and $R^{11}$ may form a ring which may contain a nitrogen, oxygen or sulfur atom together with the nitrogen atom to which $R^{10}$ and $R^{11}$ are bonded and examples of such a ring include

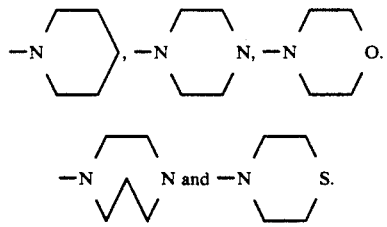

The cycloalkoxy group defined with respect to $R^2$ is one derived from the above-mentioned cycloalkyl group and examples thereof include

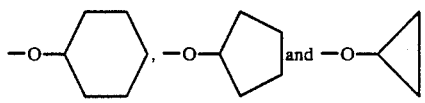

The alkenylalkyl or alkynylalkyl group defined with respect to $R^5$ and $R^6$ is one derived from the above-mentioned lower alkyl group having 1 to 6 carbon atoms in which one or two double or triple bonds are contained, and representative examples thereof include 2-propenyl group and 2-methylbutenyl group.

When $R^3$ is a hydroxyl group, the group represented by the formula:

is a carboxyl group (—COOH). $R^3$ may be a group capable of forming an ester together with the carboxyl group. Representative examples of the group include lower alkoxy groups such as methoxy group and ethoxy group and cycloalkoxy groups.

$R^5$ and $R^6$ may form a ring and examples of such a ring are as follows:

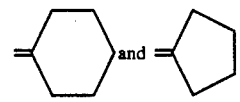

If necessary, these rings may be substituted with a lower alkyl group such as a methyl group and a halogen atom.

Further, the heteroarylalkyl group defined with respect to $R^5$ and $R^6$ is one derived from the heteroaryl group defined above with respect to $R^{10}$ and $R^{11}$ and examples thereof include pyridylmethyl group, thienylmethyl group and thienylethyl group.

The pharmacologically acceptable salt according to the present invention may be any conventional nontoxic one and examples thereof include inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate. Further, the derivative of the present invention may form a metal salt such as sodium salt, potassium salt, calcium salt and magnesium salt. The pharmacologically acceptable salt of the present invention includes these metal salts.

Although the compound of the present invention may be present as various stereoisomers because it has an asymmetric carbon atom in its molecule, it is needless to say that the present invention includes all of the isomers and mixtures of them.

Further, although some of the compounds according to the present invention are present as hydrates, it is needless to say that the present invention includes such hydrates.

Representative processes for the preparation of the compound according to the present invention will now be described, though the compound can be prepared by various processes.

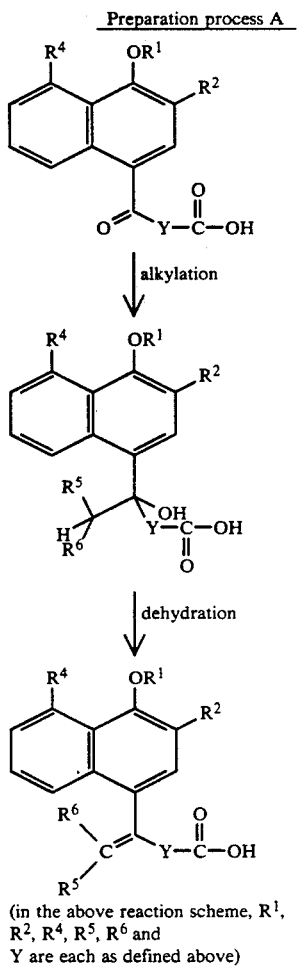

(in the above reaction scheme, $R^1$, $R^2$, $R^4$, $R^5$, $R^6$ and Y are each as defined above)

A ketocarboxylic acid represented by the general formula (II) is reacted with a Grignard reagent ($MgX$—$CHR^5R^6$) or a lithium reagent ($LiCHR^5R^6$) (wherein $R^5$ and $R^6$ are each as defined above and X represents Cl, Br or I) to give an alcohol (III). The solvent usable in this reaction includes ethers such as diethyl ether, diisopropyl ether, tetrahydrofuran, dimethoxyethane and 1,4-dioxane; benzene, toluene and hexane. The reaction temperature may range from $-78°$ C. to the boiling point of the solvent used, preferably from about $-40°$ and $30°$ C.

Then, the alcohol (III) can be converted into an objective compound (I') through dehydration in the presence of an acid. When $R^5$ is not a hydrogen atom and $R^6$ is a hydrogen atom, the dehydration gives a Z isomer preferentially, while when $R^1$ is a group removable with acid, such as a methoxymethyl group, an objective compound (I') wherein $R^1$ is a hydrogen atom simultaneously can be prepared. The solvent to be used in the dehydration includes ethers such as diethyl ether, tetrahydrofuran, 1,4-dioxane and 1,2-dimethoxyethane; benzene, toluene, xylene and dichlorobenzene. The acid to be used therein includes hydrochloric acid, sulfuric acid, p-toluenesulfonic acid, D-10-camphorsulfonic acid, methanesulfonic acid, boron trifluoride-diethyl ether complex, trifluoroacetic acid, oxalic acid and phosphoric acid. The reaction temperature may range from $-40°$ C. to the boiling point of the solvent used, preferably from room temperature to the boiling point of the solvent used.

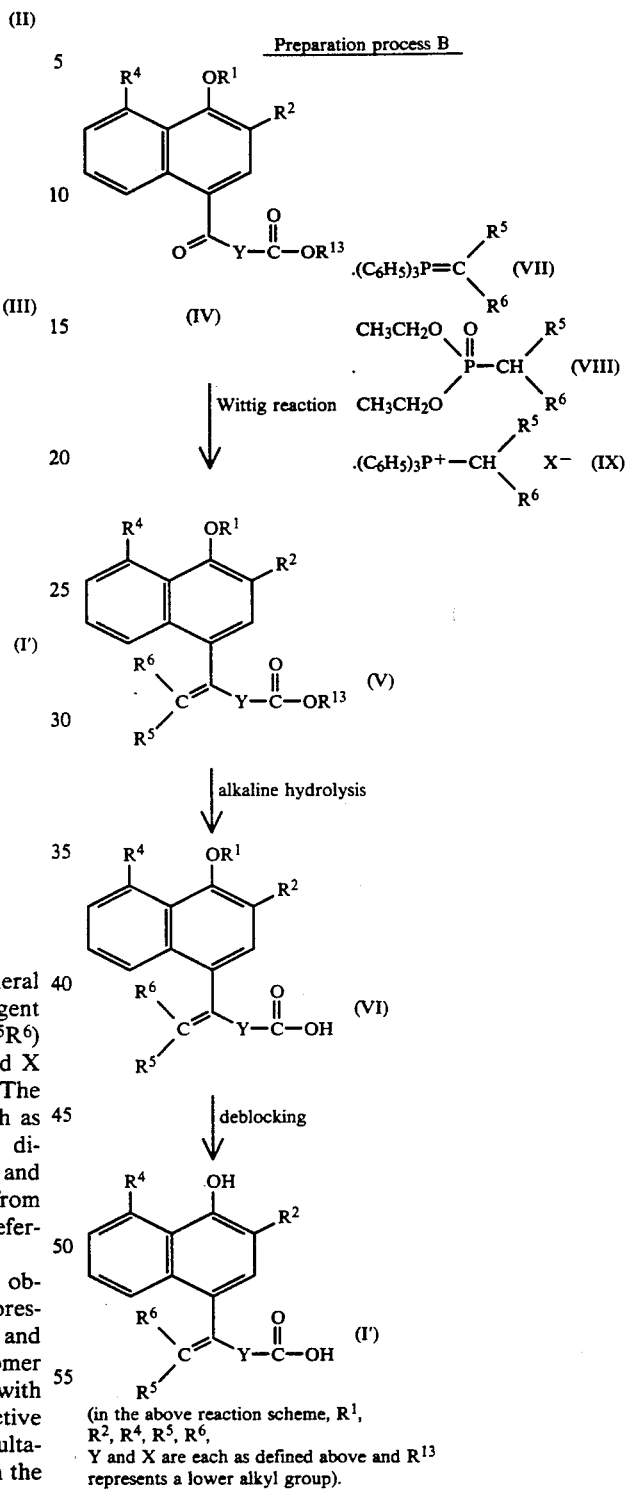

(in the above reaction scheme, $R^1$, $R^2$, $R^4$, $R^5$, $R^6$, Y and X are each as defined above and $R^{13}$ represents a lower alkyl group).

A ketoester represented by the general formula (IV) is reacted with a phosphorus compound represented by the general formula (VII), (VIII) or (IX) through Wittig reaction to give a compound (V). This reaction gives an (E) isomer preferentially when $R^5$ is a hydrogen atom and $R^6$ is not a hydrogen atom. When $R^5$ and $R^6$ are each a chlorine atom, the above reaction is conducted by the use of triphenylphosphine and carbon tetrachloride. When the reaction is conducted in the presence of a base, preferable results are obtained. The base usable therein includes sodium hydride, potassium hydride, sodium amide, sodium methoxide, sodium ethoxide, potassium t-butoxide, methyllithium and n-butyllithium. The reaction is conducted in the absence or presence of a solvent and the solvent includes alcohols such as methanol and ethanol; benzene, toluene, diethyl ether, tetrahydrofuran, 1,4-dioxane, 1,2-dimethoxyethane, N,N-dimethylformamide, acetonitrile and dimethyl sulfoxide. The reaction temperature may range from −40° C. to the boiling point of the solvent used, preferably from about 0° to 100° C.

Then, the compound (V) is hydrolyzed with a base to give a carboxylic acid (VI). The base usable in this hydrolysis includes alkali metal carbonates such as sodium carbonate and potassium carbonate; and alkali metal hydroxides such as sodium hydroxide and potassium hydroxide. The solvent to be used therein may be suitably selected from among water, methanol, ethanol, tetrahydrofuran, acetonitrile, dimethyl sulfoxide and acetone. The reaction temperature ranges from about 0° C. to the boiling point of the solvent used.

When $R^1$ is a group easily removable with acid, such as a methoxymethyl group, a compound (I') can be prepared from the compound (VI) by a conventional process. The solvent to be used in the deblocking may be suitably selected from among water, methanol, ethanol, diethylether, tetrahydrofuran, 1,4-dioxane, acetonitrile, acetone, benzene and toluene. The acid to be used therein includes hydrochloric acid, sulfuric acid, p-toluenesulfonic acid, D-10-camphorsulfonic acid, methanesulfonic acid, trifluoroacetic acid, acetic acid, boron trifluoride-ether complex, oxalic acid, phosphoric acid and so on. The reaction temperature may range from −40° C. to the boiling point of the solvent used, preferably from room temperature to the boiling point of the solvent used.

Preparation process C

A compound represented by the formula (I) wherein Z is an =$NOR^7$ group can be prepared by the following process:

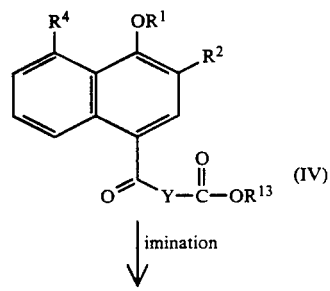

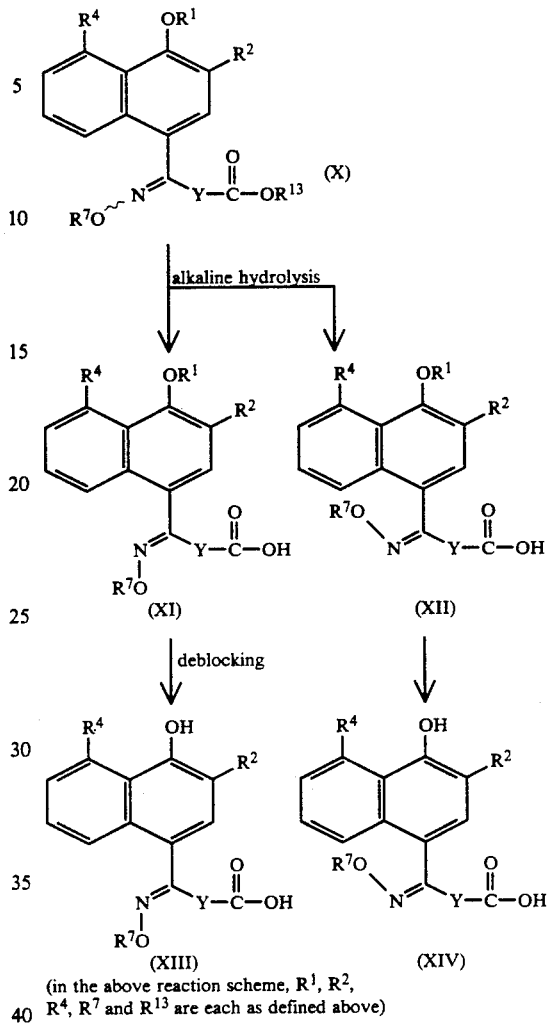

(in the above reaction scheme, $R^1$, $R^2$, $R^4$, $R^7$ and $R^{13}$ are each as defined above)

A ketoester represented by the general formula (IV) is reacted with an O-alkylhydroxylamine or a salt thereof in the presence of a base to give a compound (X) as a mixture of syn- and anti-isomers. The solvent to be used in this reaction may be suitably selected from among water, methanol, ethanol, tetrahydrofuran, 1,4-dioxane and dimethyl sulfoxide. The base usable therein includes alkali metal carbonates such as sodium carbonate and potassium carbonate; and alkali metal hydroxides such as sodium hydroxide and potassium hydroxide. The reaction temperature ranges from 0° C. to the boiling point of the solvent used.

Then, the compound (X) can be converted into a carboxylic acid according to a conventional process (similar to the one described in the Preparation process B for the conversion of (V) into (VI)). In this step, a syn-isomer (XI) and an anti-isomer (XII) can be separated from each other to give purified isomers.

When $R^1$ is a group easily removable with acid, such as a methoxymethyl group, a syn-naphthol (XIII) can be prepared from a syn-carboxylic acid (XI) according to a conventional process (similar to the one described in the Preparation process B for the conversion of (VI) into (I')).

On the other hand, an anti-naphthol (XIV) can be prepared from an anti-carboxylic acid (XII) by the action of trifluoroacetic acid without causing isomerization.

The solvent usable in this reaction includes dichloromethane, 1,2-dichloroethane, diethyl ether, tetrahydrofuran, 1,4-dioxane, 1,2-dimethoxyethane, benzene, toluene and so on. The reaction temperature ranges from 0° C. to the boiling point of the solvent used.

Preparation process D

A compound represented by the general formula (I) wherein $R^2$ is an acyl or branched alkyl group can be prepared by the following process:

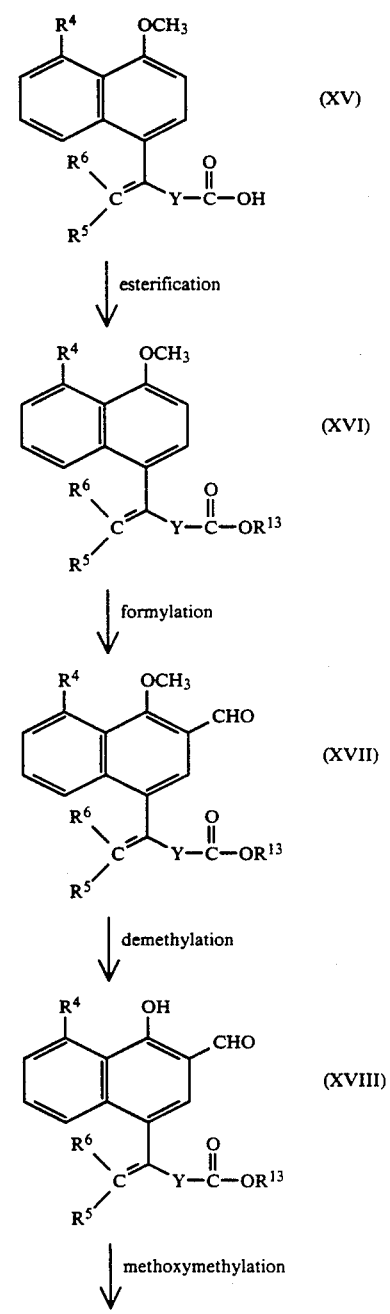

-continued
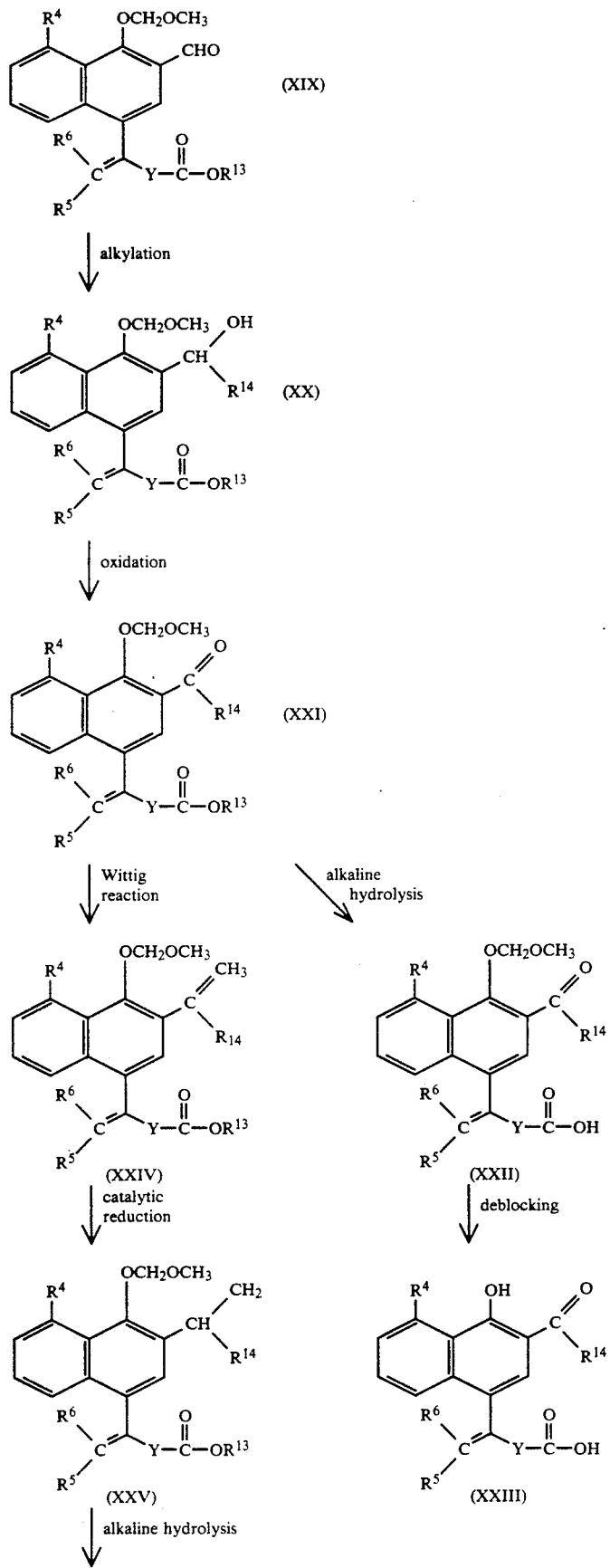

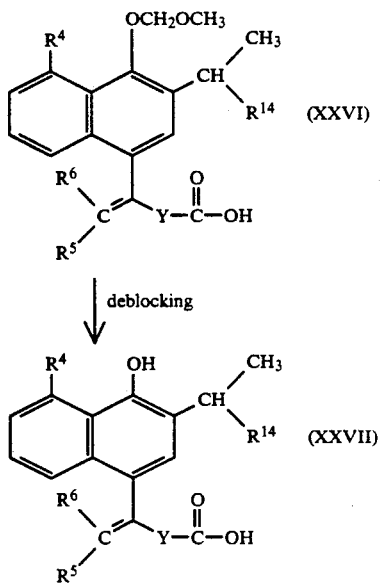

(in the above reaction scheme, $R^4$, $R^5$, $R^6$ and $R^{13}$ are each as defined above and $R^{14}$ represents a lower alkyl group).

A compound (XV) which can be prepared by the Preparation process A can be converted into an ester (XVI) according to a conventional process.

The ester (XVI) is reacted with an orthoester derivative such as methyl orthoformate and ethyl orthoformate or dichloromethyl methyl ether in the presence of a Lewis acid to give a formyl derivative (XVII). The Lewis acid usable in this step includes aluminum chloride, titanium tetrachloride and zinc chloride. The solvent to be used therein includes dichloromethane and chloroform. The reaction temperature may range from −40° C. to the boiling point of the solvent used, preferably from −10° to 40° C.

Then, the formyl derivative (XVII) is reacted with boron tribromide to give a naphthol derivative (XVIII). The solvent to be used in this reaction includes dichloromethane and chloroform and the reaction temperature ranges from −40° C. to room temperature.

The naphthol derivative (XVIII) is reacted with chloromethyl methyl ether in the presence of a base to give a methoxymethyl ether (XIX). The base to be used in this reaction includes triethylamine, N,N-diisopropylethylamine, sodium hydride, potassium tert-butoxide potassium carbonate and so on. The solvent to be used therein includes dichloromethane, tetrahydrofuran, 1,4-dioxane, 1,2-dimethoxyethane, N,N-dimethylformamide acetone and so on. The reaction temperature may range from −78° C. to the boiling point of the solvent used, preferably from −40° C. to room temperature.

Then, the compound (XIX) is reacted with an alkyllithium reagent or a Grignard reagent to give a secondary alcohol (XX). The solvent usable in this reaction includes diethylether, tetrahydrofuran, 1,4-dioxane, 1,2-dimethoxyethane, hexane, benzene, toluene and so on, and the reaction temperature ranges from −78° C. to room temperature.

The alcohol (XX) is oxidized into an acyl derivative represented by the general formula (XXI) by a conventional process. The oxidizing agent usable in this step includes manganese dioxide, pyridinium dichromate and so on. The reaction solvent includes acetone, diethylether, acetonitrile, benzene, toluene, dichloromethane, chloroform, N,N-dimethylformamide and so on. The reaction temperature may be suitably selected within a range of from the temperature attained under cooling with ice to the boiling point of the solvent used.

The acyl derivative (XXI) can be hydrolyzed with an alkali and freed of the protective group in a similar manner to the one described in the Preparation process B for the conversion of (V) through (VI) into (I') to give a carboxylic acid represented by the general formula (XXIII).

Alternatively, the acyl derivative (XXI) is reacted with a phosphorus compound represented by the general formula (VII), (VIII) or (IX) wherein $R^5$ and $R^6$ are each a hydrogen atom through Wittig reaction according to a conventional process to give a compound (XXIV). The solvent, temperature and base to be employed in this reaction are each as described in the Preparation process B for the conversion of (IV) into (V).

The compound (XXIV) is catalytically reduced into a compound (XXV) in a hydrogen atmosphere of about 1 atm according to a conventional process. The catalyst to be used in this reduction includes palladium-carbon, platinum oxide, Raney nickel and so on. The solvent to be used therein may be suitably selected from among water, methanol, ethanol, propanol, ethyl acetate, tetrahydrofuran, 1,4-dioxane and acetic acid. The reaction mixture ranges from 0° C. to room temperature.

Further, the compound (XXV) is converted into a carboxylic acid represented by the general formula (XXVII) in a similar manner to that described in the Preparation process B for the conversion of (V) through (VI) into (I').

Preparation process E

A compound represented by the general formula (I) or (XIII) wherein $R^1$ is an acyl group can be prepared by the following process:

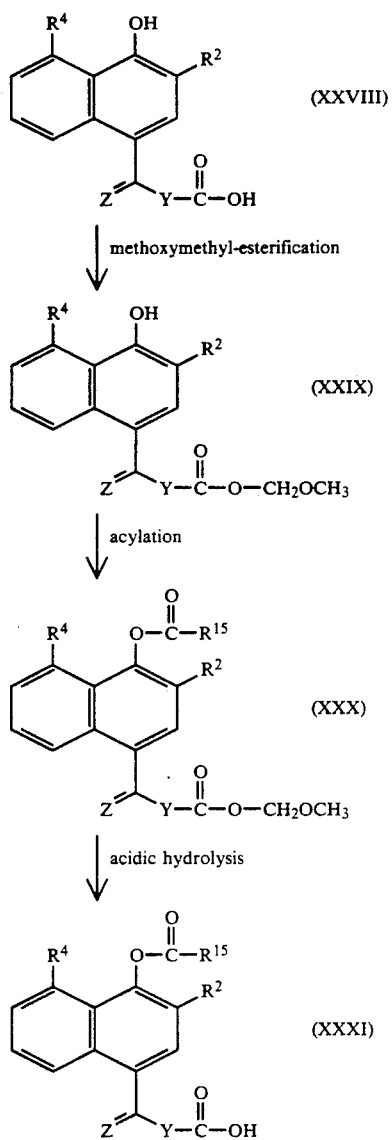

(in the above reaction scheme, $R^2$, $R^4$, Y and Z are each as defined above and $R^{15}$ represents a lower alkyl group).

That is, a compound (XXVIII) is reacted with chloromethyl methyl ether in the presence of a base to give a methoxymethyl ester (XXIX). The base usable in this reaction includes triethylamine, N,N-diisopropylethylamine, potassium carbonate and so on, while the solvent usable therein includes dichloromethane, chloroform, diethylether, 1,4-dioxane, 1,2-dimethoxyethane, N,N-dimethylformamide, acetone and so on. The reaction is conducted at a temperature ranging from −40′ C. to the boiling point of the solvent used, preferably under cooling with ice.

Then, the methoxymethyl ester (XXIX) is reacted with an acyl chloride in the presence of a base to give a compound (XXX). The base usable in this step includes triethylamine, N,N-diisopropylethylamine, sodium hydride, potassium tert-butoxide and so on, while the solvent to be used therein may be suitably selected from among dichloromethane, chloroform, diethylether, 1,4-dioxane, 1,2-dimethoxyethane and N,N-dimethylformamide. The reaction may be conducted at a temperature ranging from −40° C. to room temperature, preferably under cooling with ice.

The compound (XXX) can be easily converted into a compound (XXXI) through deblocking in a similar manner to the one described in the Preparation process B for the conversion of (VI) into (I′).

Preparation Process for Starting Material: A

Among the compounds represented by the general formula (II) or (IV) which are each used as a starting material in the above-mentioned Preparation process A, B or C, a compound wherein $R^2$ is a lower alkoxy group, a lower branched alkoxy group or a cyloalkoxy group can be prepared by, for example, the following process:

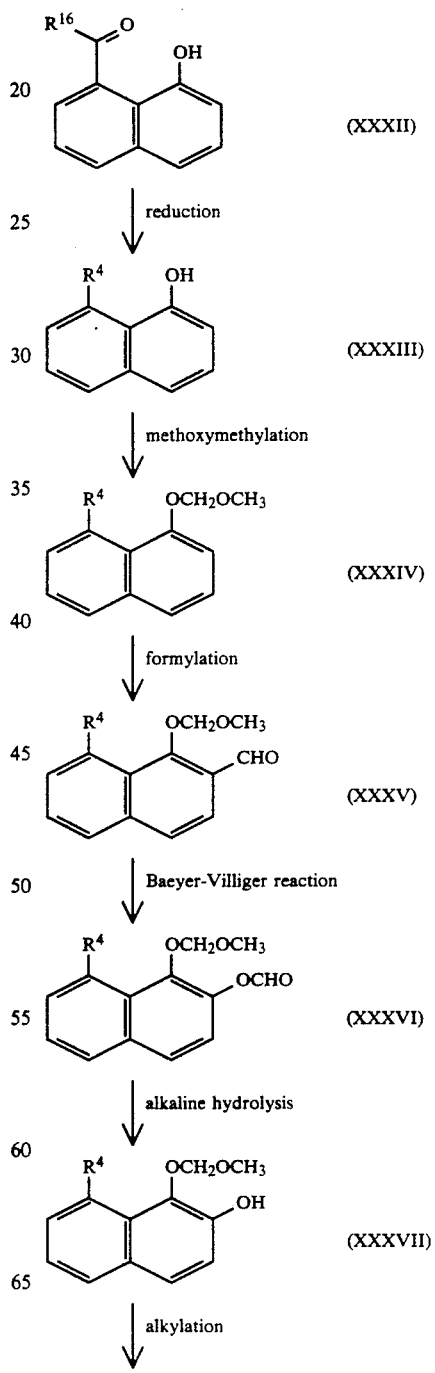

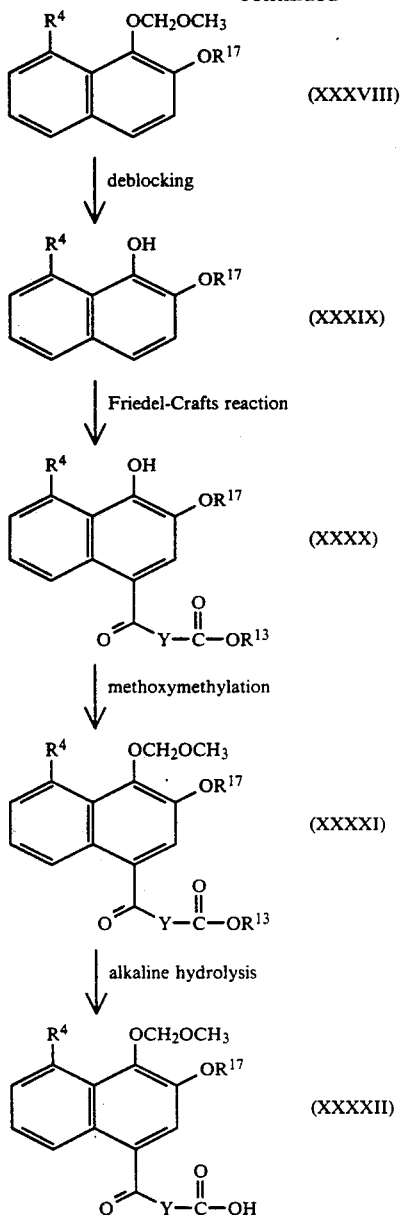

(in the above reaction scheme, $R^4$, $R^{13}$ and Y are each as defined above; $R^{16}$ represents an aryl group, an arylalkyl group or an alkyl group; and $R^{17}$ represents an alkyl group or a cycloalkyl group)

That is, a known compound (XXXII) [see R. J. Packer et al., J. Chem. Soc., (C), 2194(1967)] is reduced with hydrazine or hydrazine hydrate and sodium hydroxide to give a naphthol derivative (XXXIII). In this step, a semicarbazone can be used instead of hydrazine and potassium hydroxide or sodium ethoxide can be used instead of sodium hydroxide. The solvent usable in this reduction includes diethylene glycol, triethanolamine and so on, and the reaction temperature ranges from 80° C. to the boiling point of the solvent used.

The naphthol derivative (XXXIII) is reacted with chloromethyl methyl ether in the presence of a base to give a methoxymethyl ether (XXXIV). The base usable in this reaction includes triethylamine, N,N-diisopropylethylamine, sodium hydride, potassium tert-butoxide, potassium carbonate and so on. The solvent to be used therein incudes dichloromethane, tetrahydrofuran, 1,4-dioxane, 1,2-dimethoxyethane, N,N-dimethylformamide, acetone and so on. The reaction temperature may range from −78° C. to the boiling point of the solvent used, preferably from −40° C. to room temperature.

The methoxymethyl ether (XXXIV) is reacted with a strong base such as n-butyllithium and then with N,N-dimethylformamide to give an aldehyde (XXXV). The reactions are conducted in an etheric solvent such as ether and tetrahydrofuran at a temperature ranging from −78° to 30° C., preferably from −30° C. to room temperature.

The aldehyde (XXXV) can be oxidized with hydrogen peroxide, or a peracid such as peracetic acid and m-chloroperbenzoic acid to give a formate (XXXVI). The solvent to be used in this oxidation may be suitably selected from among water, dichloromethane, chloroform, acetic acid and so on.

The formate (XXXVI) can be hydrolyzed with an alkali according to a conventional process to give a 2-naphthol derivative (XXXVII).

The naphthol derivative (XXXVII) is reacted with an alkyl halide or a sulfonate ester in the presence of a base, for example, an alkali metal carbonate such as sodium carbonate and potassium carbonate or an alkali metal hydride such as sodium hydride. The halogen constituting the alkyl halide includes chlorine, bromine and iodine. The solvent to be used in this step includes ketones such as acetone and methyl ethyl ketone; N,N-dimethylformamide, dimethyl sulfoxide and tetrahydrofuran.

The obtained alkoxynaphthalene (XXXVIII) can be deblocked with hydrochloric acid, sulfuric acid or p-toluenesulfonic acid by a conventional process to give a 1-naphthol derivative (XXXIX).

The naphthol derivative (XXXIX) is reacted with ethyloxalyl chloride, ethylmalonyl chloride or ethylsuccinyl chloride to give a ketoester represented by the general formula (XXXX). The catalyst to be used in this reaction includes aluminum chloride, titanium tetrachloride, zinc chloride and so on. The solvent to be used therein includes dichloromethane, chloroform, benzene, toluene and so on.

The ketoester (XXXX) is reacted with chloromethyl methyl ether in the presence of a base such as triethylamine, N,N-diisopropylethylamine, sodium hydride and potassium carbonate by a conventional process to give a methoxymethyl derivative represented by the general formula (XXXXI). The solvent usable in this reaction is one inert to the reaction, for example dichloromethane, chloroform, diethylether, tetrahydrofuran, N,N-dimethylformamide or acetone. The reaction temperature may range from −40° C. to the boiling point of the solvent used, preferably from about 0° C. to room temperature.

The obtained ester (XXXXI) can be hydrolyzed with a base such as sodium hydroxide and potassium hydroxide by a conventional process to give a carboxylic acid (XXXXII). The solvent to be used in this hydrolysis may be suitably selected from among water, ethanol, methanol, tetrahydrofuran, dimethyl sulfoxide and so on. The reaction temperature may range from −40° to 80° C., preferably from about 0° C. to room temperature.

Preparation process for starting material: B

Among the compounds represented by the general formula (II) or (IV) which are each used as a starting material in the above-mentioned Preparation process A, B or C, a compound wherein $R^2$ is a lower alkyl group can be prepared from a compound (XXXIV) which can be prepared by the above-mentioned Preparation process A for starting material by the following process:

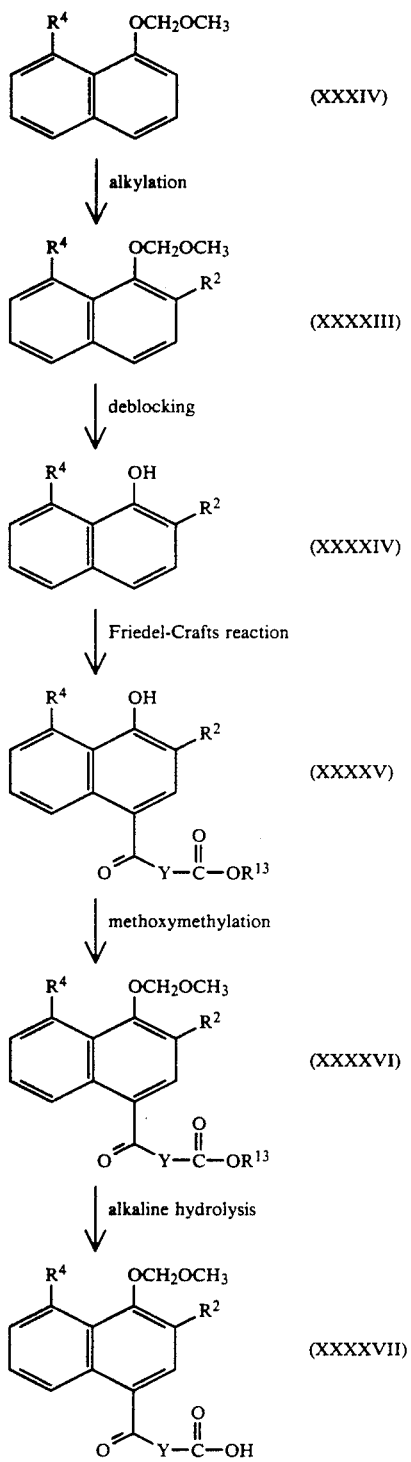

(in the above reaction scheme, $R^4$, $R^{13}$ and Y are each as defined above and $R^2$ represents a lower alkyl group).

That is, a compound (XXXIV) is reacted with n-butyllithium and then with an alkyl halide in the presence of tetramethylethylenediamine to give an alkylate (XXXXIII). The reaction is conducted in an etheric solvent such as ether and tetrahydrofuran at a temperature ranging from $-78°$ to $30°$ C., preferably from $-30$ to room temperature.

The preparation of a compound (XXXXVII) from the alkylate (XXXIII) can be conducted in a similar manner to that described in the above-mentioned Preparation process A for starting material.

Preparation process for starting compound: C

The compound used in the above-mentioned Preparation process D can be prepared by the following process:

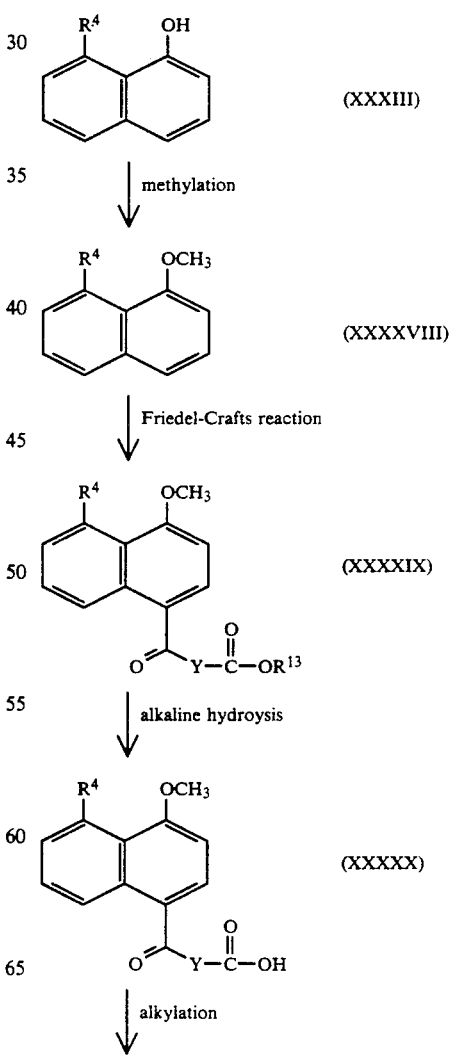

-continued

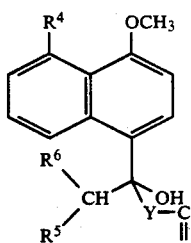
(XXXXXI)

↓ dehydration

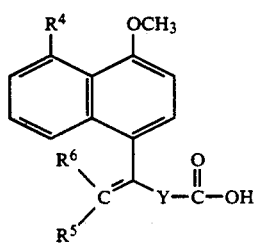
(XV)

(in the above reaction scheme, $R^4$, $R^5$, $R^6$, $R^{13}$ and Y are each as defined above).

That is, a methoxy derivative (XXXXVIII) can be prepared by reacting a naphthol derivative (XXXIII) which can be prepared by the above-mentioned Preparation process A for starting material with methy iodide in the presence of a base. The base usable in this reaction includes alkali metal carbonates such as sodium carbonate and potassium carbonate; triethylamine, N,N-diisopropylethylamine, sodium hydride and potassium tert-butoxide. The solvent to be used therein includes acetone, methyl ethyl ketone, tetrahydrofuran, N,N-dimethylformamide, dimethyl sulfoxide, dichloromethane, chloroform and so on.

The preparation of a compound (XXXXX) from the methoxy derivative (XXXXVIII) can be conducted in a similar manner to that described in the Preparation process A for starting material A.

The conversion of the compound (XXXXX) into a compound (XV) can be conducted in a similar manner to that described in the Preparation process A.

In the present invention, the intermediates (naphthalene derivatives) defined by the following general formula (A) are novel compounds.

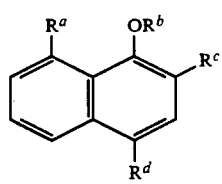
(A)

wherein $R^a$ means a benzyl group, $R^b$ stands for a hydrogen atom or a lower alkyl group, $R^c$ stands for a hydrogen atom or a lower alkyl group and $R^d$ represents a hydrogen atom or a group represented by the formula:

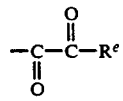

(wherein $R^e$ stands for a hydroxyl group or a lower alkyl group).

Among these naphthalene derivatives, the compounds defined by the following formulae are important as intermediate, which will be explained in the referencial examples 1, 12 and 22, to prepare the compounds in the present invention.

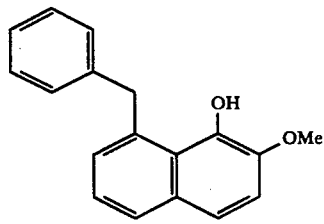

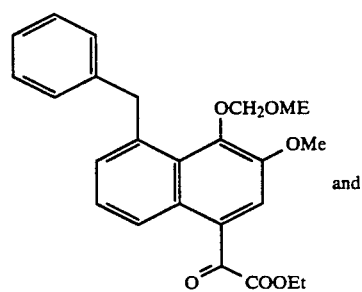
and

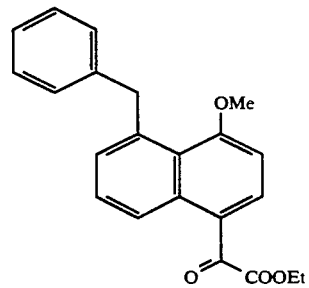

EXAMPLES

Pharmacological Experimental Examples will now be described in order to illustrate the effects of the present invention.

EXPERIMENTAL EXAMPLES

Activity against the $PGE_2$ production from cultured synovial cell of rat

A synovial membrane taken out of the knee joint of a Lewis male rat was treated with collagenase-trypsin to separate off synovial cells. A test compound was added to a system prepared by the subculture of the synovial cells. The cells were stimulated with a neutrophil-originating factor (IL-1-like factor) to induce $PGE_2$ production. After one day, the amount of $PGE_2$ liberated into the culture medium was determined by radioimmunoassay (see R. Hashida et al., Prostaglandins, 27 (1984), 697).

Activity against LTB₄ production from human neutrophil

A test compound was added to a suspension of neutrophil separated from the human peripheral blood and the obtained mixture was preincubated at 37° C. for 5 minutes, followed by the addition of calcium ionophore A23187 in an amount of 2 μg/ml. After 10 minutes, the obtained mixture was cooled to stop the reaction. The amount of $LTB_4$ contained in the supernatant of the reaction mixture was determined by radioimmunoassay (see H. Shirota et al., Arzneim Forsol Drug Res., 37 (1987) 930).

The representative results of the experiment are given in Table 1.

TABLE 1

| Example No. | Inhibitory activity against $PGE_2$ production from synovial cells of rat $IC_{50}$ (μM) | Inhibitory activity against $LTB_4$ production from human neutrophil $IC_{50}$ (μM) |
|---|---|---|
| 1 | 0.42 | 0.51 |
| 2 | 0.62 | 0.32 |
| 3 | 1.45 | 0.52 |
| 4 | 2.76 | 1.68 |
| 5 | 1.64 | 0.51 |
| 7 | 3.10 | >10 |
| 10 | 2.10 | 1.86 |
| 11 | 1.88 | 1.09 |
| 12 | 3.54 | 10 |
| 13 | 3.35 | 0.83 |
| 14 | 3.23 | 0.72 |
| 15 | 1.07 | 0.73 |
| 40 | 2.04 | 3.16 |
| 55 | 0.28 | 2.35 |

It can be understood from the results that the compound of the present invention has an inhibitory activity against the production of two mediators, i.e., prostaglandin (PG) and leukotriene (LT).

With respect to inflammatory reactions, it is known that $PGE_2$ produced by the arachidonate cascade is a main substance causative of pyrexia, sore, swelling and other symptoms and it is also well known that the antiinflammatory mechanism of many current nonsteroidal anti-inflammatory drugs resides mainly in the inhibition of cycloxygenase.

On the other hand, a lipoxygenase system is believed to participate significantly in inflammation, because $LTB_4$ causes the migration, aggregation, adherence and/or degranulation of leukocyte and $LTC_4$ and $D_4$ enhance the permeability of vessel. It has been clinically ascertained that the $LTB_4$ concentration in the synovial fluid of a patient with rheumatoid arthritis is high and the 5-lipoxygenase activity of the articular tissues of such a patient is extremely high (see F. Hirata et al., Proc. Natl. Acad. Sci., 78 (1981) 3190).

Accordingly, the compounds of the present invention characterized by being capable of inhibiting LT production at a concentration capable of inhibiting PG production is extremely useful as an anti-inflammatory drug.

That is, the compounds of the present invention are efficacious not only in the resolution and pain-killing of chronic rheumatoid arthritis, osteoarthritis, shoulder periarthritis, cervicobrachial syndrome, lumbago and so on and postoperative and posttraumatic resolution and pain-killing, but also in the treatment of inflammation in which LT participates.

In addition, the compounds of the present invention are effective in treating diseases for which the above-mentioned inhibitory activity against the production of prostaglandin (PG) and leukotriene (LT) is efficacious.

When the compounds of the present invention are used as therapeutic and preventive agents for these diseases, they may be each administered orally as a tablet, powder, granule, capsule or syrup, or parenterally as a suppository, injection, external preparation or drop. Oral administration is preferable.

The dose of the compound remarkably varies depending upon the kind and symptom of disease and the age of a patient. When it is orally administered to a human being, it is 0.01 to 20 mg/kg, preferably 0.1 to 15 mg/kg, still preferably 1 to 10 mg/kg, which may be administered in 1 to 3 portions a day.

The compounds of the present invention can be each converted into a drug for oral or parenteral administration by the use of a conventional pharmacologically acceptable carrier according to a conventional process.

An injection or drop according to the present invention is prepared by adding a pH modifier, buffer, stabilizer and/or solubilizing agent at need to an active ingredient, followed by freeze drying at need, and converting the obtained mixture into a subcutaneous, intramuscular or intravenous injection or a drop by a conventional process.

EXAMPLE

Examples will now be described in order to illustrate the compounds of the present invention and the process for the preparation thereof in more detail, though the present invention is not limited to them.

The preparation of the starting compounds used in Examples will be described in Referential Examples.

In the Referential Examples and Examples which follow, Me stands for a methyl group, Et an ethyl group and Ac an acetyl group.

note 1) in some cases, no peak assignable to carboxylic acid was detected in nuclear magnetic resonance spectroscopy.

note 2) each melting point was determined with a micro melting point apparatus (mfd. by Yanagimoto Seisakusho).

REFERENTIAL EXAMPLE 1

8-Benzyl-2-methoxy-1-naphthol

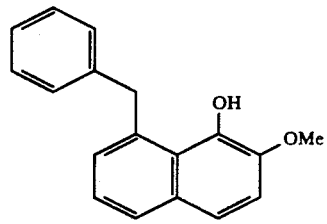

(a) synthesis of 8-benzyl-1-naphthol

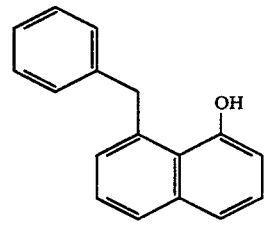

122 g of 8-benzoyl-1-naphthol was suspended in 800 ml of diethylene glycol, followed by the addition of 250 ml of hydrazine monohydrate and 99 g of sodium hydroxide at room temperature. The obtained mixture was stirred at 100° C. for 48 hours and cooled to room temperature by allowing to stand, followed by the addition of 500 ml of water. The obtained mixture was acidified with concentrated hydrochloric acid and extracted with 1.5 l of toluene. The organic layer was washed with a saturated aqueous solution of sodium chloride and purified by silica gel column chromatography (developer: benzene) to give 100 g of the title compound as a pale-yellow crystal.

m.p.: 67° to 71° C.

¹H-NMR (90 MHz, CDCl₃) δ: 4.67 (s, 2H), 5.08 (s, 1H), 6.54 (dd, J=7.2 Hz, 1.4 Hz, 1H), 6.80~7.50 (m, 9H), 7.61 (dd, J=7.2 Hz, 1.4 Hz, 1H).

(b) synthesis of 8-benzyl-1-methoxymethoxynaphthalene

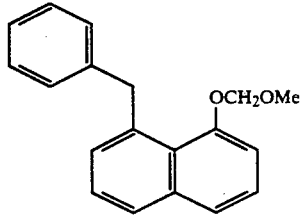

100 g of 8-benzyl-1-naphthol was dissolved in 300 ml of N,N-dimethylformamide to give a solution. 18.6 g of sodium hydride (55% suspension in oil) was added to the solution under cooling with ice. After 30 minutes, 34.4 g of chloromethyl methyl ether was added to the obtained mixture under cooling with ice, followed by stirring for 10 minutes. The obtained mixture was further stirred at room temperature for 30 minutes. The resulting reaction mixture was poured onto ice-water and the obtained mixture was extracted with 1.2 l of ethyl acetate. The organic layer was washed with a saturated aqueous solution of sodium chloride, dried over anhydrous magnesium sulfate and concentrated in a vacuum. The obtained residue was purified by silica gel column chromatography (developer: hexane to 9% ethyl acetate/hexane) to give 103 g of the title compound as a yellow oil.

¹H-NMR (90 MHz, CDCl₃) δ: 3.11 (s, 3H), 4.65 (br s, 2H), 4.96 (s, 2H), 6.8~7.55 (m, 10H), 7.65 (dd, J=7.2 Hz, 1.8 Hz, 1H).

(c) synthesis of 8-benzyl-1-methoxymethoxy-2-naphthaldehyde

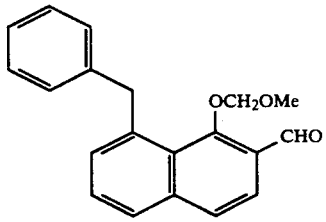

103 g of 8-benzyl-1-methokymethoxynaphthalene was dissolved in 300 ml of anhydrous ether to give a solution. 190 ml of a 2.5M n-butyllithium solution (in hexane) was dropped into the solution under cooling with ice in a nitrogen atmosphere. The obtained mixture was stirred at room temperature for 2 hours and cooled to −40° C., followed by the dropwise addition of 44 ml of anhydrous N,N-dimethylformamide. The temperature of the reaction mixture was raised again to room temperature, followed by the addition of 100 ml of water. The obtained mixture was extracted with ethyl acetate. The organic layer was washed with water, dried over anhydrous magnesium sulfate and concentrated in a vacuum. The residue was purified by silica gel column chromatography (developer: 5 to 20% ethyl acetate/hexane) to give 110 g of the title compound as a yellow oil.

¹H-NMR (90 MHz, CDCl₃) δ: 3.44 (s, 3H), 4.70 (br s, 2H), 4.82 (s, 2H), 6.85~7.80 (m, 9H), 7.80 (d, J=7.9 Hz, 1H), 10.10 (br s, 1H).

(d) synthesis of 8-benzyl-1-methoxymethoxy-2-naphthyl formate

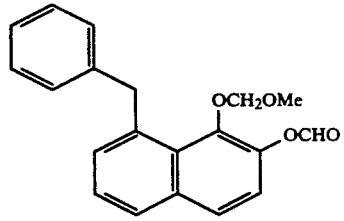

96 g of 8-benzyl-1-methoxymethoxy-2-naphthaldehyde was dissolved in 500 ml of dichloromethane to give a solution. 76.4 g of 85% m-chloroperbenzoic acid was gradually added to the solution at room temperature. The obtained reaction mixture was heated under reflux for one hour, cooled by allowing to stand and further cooled with ice. The resulting mixture was filtered to remove insolubles. The filtrate was washed with an aqueous solution of sodium thiosulfate, a saturated aqueous solution of sodium hydrogen-carbonate and a saturated aqueous solution of sodium chloride successively, dried over anhydrous magnesium sulfate and concentrated in a vacuum. The obtained residue was used in the subsequent reaction without being purified.

(e) synthesis of 8-benzyl-1-methoxymethoxy-2-naphthol

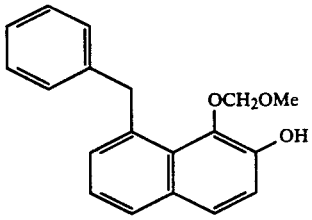

The formate prepared in the step (d) was dissolved in 300 ml of methanol, followed by the addition of 43 g of potassium carbonate. The obtained mixture was stirred at room temperature for 30 minutes and filtered to remove insolubles. The filtrate was concentrated in a vacuum. 400 ml of water was added to the residue. The obtained mixture was neutralized with concentrated hydrochloric acid and extracted with ethyl acetate. The organic layer was washed with water twice, dried over anhydrous magnesium sulfate and concentrated in a vacuum to give a brown oil. The oil was purified by silica gel column chromatography (developer: 5% ethyl acetate/hexane) to give 63 g of the title compound as a colorless crystal.

m.p.: 54° to 57.5° C.

¹H-NMR (400 MHz, CDCl₃) δ: 3.54 (s, 3H), 4.47 (s, 2H), 4.66 (s, 2H), 7.06 (br d, J=7.3 Hz, 2H), 7.16 (br t, J=7.3 Hz, 1H), 7.20 (dd, J=7.9 Hz, 1.5Hz, 1H), 7.20~7.30 (m, 1H), 7.22 (d, J=8.8 Hz, 1H), 7.25 (br t, J=7.3 Hz, 2H), 7.58 (d, J=8.8 Hz, 1H), 7.68 (dd, J=7.9 Hz, 1.5 Hz, 1H), 8.16 (s, 1H).

(f) synthesis of 8-benzyl-2-methoxy-1-methoxymethoxy-naphtalene

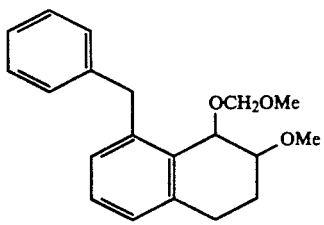

82.7 g of 8-benzyl-1-methoxymethoxy-2-naphthol was dissolved in 300 ml of N,N-dimethylformamide to give a solution. 12.3 g of sodium hydride (55% suspension in oil) was added to the solution at room temperature. The obtained mixture was stirred for 30 minutes, followed by the dropwise addition of 17.5 ml of methyl iodide. The obtained mixture was stirred for one hour and poured onto ice-water. The obtained mixture was extracted with ethyl acetate. The organic layer was washed with a saturated aqueous solution of sodium chloride, dried over anhydrous magnesium sulfate and concentrated in a vacuum. The obtained residue was purified by silica gel column chromatography (developer: 3 to 9% ethyl acetate/hexane) to give 79.5 g of the title compound as a yellow oil.

¹H-NMR (400 MHz, CDCl₃) δ: 3.50 (s, 3H), 3.94 (s, 3H), 4.82 (s, 2H), 5.10 (s, 2H), 7.10~7.40 (m, 8H), 7.55~7.65 (m, 2H).

(g) synthesis of 8-benzyl-2-methoxy-1-naphthol

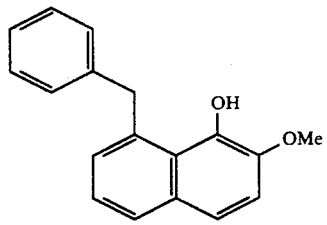

79.5 g of 8-benzyl-2-methoxy-1-methoxymethoxynaphthalene was dissolved in 300 ml of acetone to give a solution. 120 ml of 6N hydrochloric acid was added to the solution at room temperature. The obtained mixture was stirred for 1.5 hours, followed by the addition of 400 ml of water. The obtained mixture was extracted with ethyl acetate. The organic layer was washed with water, dried over anhydrous magnesium sulfate and distilled in a vacuum to remove the solvent. The obtained solid was washed with hexane/diisopropyl ether (1:1) to give 51 g of the title compound as a colorless crystal.

m.p.: 84° to 86° C.

¹H-NMR (400 MHz, CDCl₃) δ: 3.95 (s, 3H), 4.77 (br s, 2H), 6.25 (s, 1H), 7.20~7.60 (m, 8H), 7.39 (d, J=9.0 Hz, 1H), 7.62 (br d, J=8.0 Hz, 1H).

REFERENTIAL EXAMPLES 2 TO 5

The following compounds were each prepared in a similar manner to that of the Referential Example 1 except that the methyl iodide used in the step (f) was replaced by ethyl iodide, propyl iodide, isopropyl iodide or bromocyclopentane:

8-benzyl-2-ethoxy-1-naphthol
8-benzyl-2-propoxy-1-naphthol
8-benzyl-2-isopropoxy-1-naphthol
8-benzyl-2-cyclopentyloxy-1-naphthol.

REFERENTIAL EXAMPLE 6

8-Benzyl-2-methyl-1-naphthol

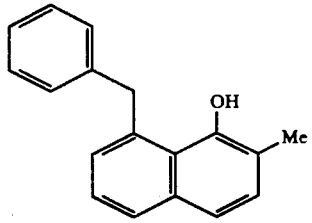

10 g of 8-benzyl-1-methoxymethoxynaphthalene was dissolved in 100 ml of anhydrous ether, followed by the addition of 6.5 ml of tetramethylethylenediamine. 27 ml of a 1.6M solution of n-butyllithium in hexane was dropped into the obtained mixture under cooling with ice. The obtained mixture was stirred at 0° C. for one hour, followed by the dropwise addition of 2.7 ml of methyl iodide. The obtained mixture was stirred at room temperature for one hour and poured into a saturated aqueous solution of ammonium chloride. The obtained mixture was extracted with ethyl acetate. The organic layer was dried over anhydrous magneisum sulfate and distilled in a vacuum to remove the solvent. The residue was dissolved in 150 ml of acetone, followed by the addition of 60 ml of 6N hydrochloric acid. The obtained mixture was stirred at room temperature for one hour, followed by the addition of water. The obtained mixture was extracted with ethyl acetate. The organic layer was dried over anhydrous magnesium sulfate and distilled in a vacuum to remove the solvent. The residue was purified by silica gel column chromatography (developer: 3% ethyl acetate/hexane) to give 6 g of the title compound as a yellow oil.

¹H-NMR (400 MHz, CDCl₃) δ: 2.31 (s, 3H), 4.64 (s, 2H), 5.00 (s, 1H), 7.05~7.32 (m, 7H), 7.33 (t, J=8.0 Hz, 1H), 7.28 (d, J=8.0 Hz, 1H), 7.68 (d, J=8.0 Hz, 1H).

REFERENTIAL EXAMPLES 7 TO 9

The following compounds were each prepared in a similar manner to that of the Referential Example 6 except that the methyl iodide was replaced by ethyl iodide, propyl iodide or butyl iodide:

8-benzyl-2-ethyl-1-naphthol
8-benzyl-2-propyl-1-naphthol
8-benzyl-2-butyl-1-naphthol.

REFERENTIAL EXAMPLE 10

8-Benzyl-1-methoxynaphthalene

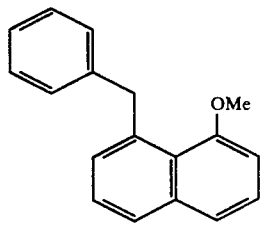

100 g of 8-benzyl-1-naphthol was dissolved in 300 ml of N,N-dimethylformamide to give a solution. 24.2 g of sodium hydride (55% suspension in oil) was added to the solution under cooling with ice. The obtained mixture was stirred at room temperature for 30 minutes. Methyl iodide was added to the resulting mixture under cooling with ice. The obtained mixture was stirred for 30 minutes under cooling with ice and poured onto ice-water. The obtained mixture was extracted with ethyl acetate. The organic layer was washed with a saturated aqueous solution of sodium chloride twice, dried over anhydrous magnesium sulfate and distilled in a vacuum to remove the solvent. The residue was purified by silica gel column chromatography (developer: 5% ethyl acetate/hexane) to give 73 g of the title compound.

$^1$H-NMR (400 MHz, CDCl$_3$) δ: 3.70 (s, 3H), 4.69 (s, 2H), 6.76 (d, J=8.0 Hz, 1H), 7.08 (d, J=8.0 Hz, 2H), 7.10~7.28 (m, 4H), 7.37 (t, J=8.0 HZ, 1H), 7.37 (t, J=8.0 Hz, 1H), 7.43 (d, J=8.0 Hz, 1H), 7.70 (d, J=8.0 Hz, 1H).

REFERENTIAL EXAMPLE 11

2-Methoxy-8-pentyl-1-naphthol

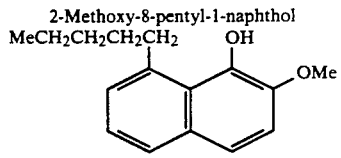

The title compound was prepared from 8-pentanoyl-1-naphthol in a similar manner to that of the Referential Example 1.

REFERENTIAL EXAMPLE 12

Ethyl 2-(5-benzyl-3-methoxy-4-methoxymethoxy-1-naphthyl)-2-oxo-acetate

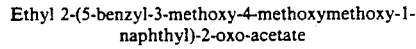

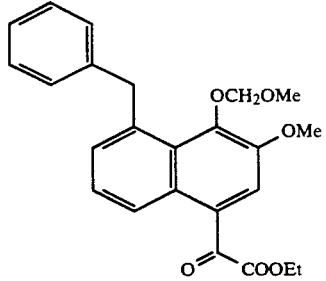

(a) synthesis of ethyl 2-(5-benzyl-4-hydroxy-3-methoxy-1-naphthyl)-2-oxo-acetate

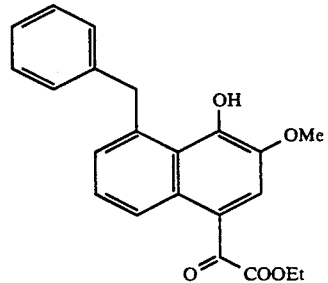

64 g of anhydrous aluminum chloride was suspended in 500 ml of dichloromethane. 40.3 ml of ethyloxalyl chloride was added to the suspension at room temperature. A solution of 63.4 g of 8-benzyl-2-methoxy-1-naphthol in 300 ml of dichloromethane was dropped into the obtained mixture under cooling with ice. The obtained mixture was stirred for 30 minutes under cooling with ice and poured onto 1 l of ice-water. The organic layer was washed with water, dried over anhydrous magnesium sulfate and distilled in a vacuum to remove the solvent. The obtained solid was washed with diisopropyl ether to give 54 g of the title compound as a yellow crystal.

m.p.: 124° to 126° C.

$^1$H-NMR (400 MHz, CDCl$_3$) δ1.44 (t, J=7.1 Hz, 3H), 3.98 (s, 3H), 4.47 (q, J=7.1 Hz, 2H), 4.76 (s, 2H), 7.00 (s, 1H), 7.09 (br d, J=8.2 Hz, 2H), 7.15 (br t, J=8.2 Hz, 1H), 7.24 (br t, J=8.2 Hz, 2H), 7.30 (dd, J=7.0 Hz, 1.1 Hz, 1H), 7.51 (dd, J=8.8 Hz, 7.0 Hz, 1H), 7.74 (s, 1H), 9.03 (dd, J=8.8 Hz, 1.1 Hz, 1H).

(b) synthesis of ethyl 2-(5-benzyl-3-methoxy-4-methoxymethoxy-1-naphthyl)-2-oxo-acetate

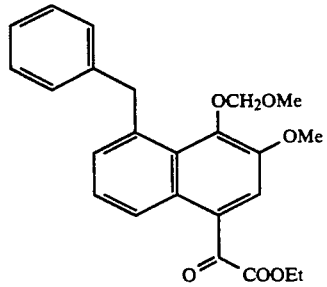

5.0 g of the naphthol prepared in the step (a) was dissolved in 100 ml of dichloromethane to give a solution. 7.4 ml of N,N-diisopropylethylamine and 2.2 ml of chloromethyl methyl ether were added to the solution successively at room temperature. The obtained mixture was stirred for 30 minutes and washed with dilute hydrochlopic acid, water, a saturated aqueous solution of sodium hydrogencarbonate and water successively. The organic layer was dried over anhydrous magnesium sulfate and distilled in a vacuum to remove the solvent. 5.2 g of the title compound was obtained as a yellow crystal.

m.p.: 70° to 72° C.

$^1$H-NMR (400 MHz, CDCl$_3$) δ: 1.44 (t, J=7.1 Hz, 3H), 3.38 (s, 3H), 3.92 (s, 3H), 4.48 (q, J=7.1 Hz, 2H), 4.80 (br s, 2H), 5.20 (s, 2H), 7.09 (br d, J=7.5 Hz, 2H), 7.16 (br t, J=7.5 Hz, 1H), 7.24 (br t, J=7.5 Hz, 2H), 7.28 (dd, J=7.1 Hz, 1.1 Hz, 1H), 7.46 (dd, J=8.8 Hz, 7.1 Hz, 1H), 7.77 (s, 1H), 8.86 (dd, J=8.8 Hz, 1.1 Hz, 1H).

REFERENTIAL EXAMPLES 13 TO 21

The following compounds were prepared respectively from the compounds prepared in the Referential Examples 2 to 9 and 11 in a similar manner to that of the Referential Example 12:

ethyl 2-(5-benzyl-3-ethoxy-4-methoxymethoxy-1-naphthyl)-2-oxo-acetate
ethyl 2-(5-benzyl-4-methoxymethoxy-3-propoxy-1-naphthyl)-2-oxo-acetate
ethyl 2-(5-benzyl-3-isopropoxy-4-methoxymethoxy-1-naphthyl)-2-oxo-acetate
ethyl 2-(5-benzyl-3-cyclopentyloxy-4-methoxymethoxy-1-naphthyl)-2-oxo-acetate
ethyl 2-(5-benzyl-4-methoxymethoxy-3-methyl-1-naphthyl)-2-oxo-acetate ethyl 2-(5-benzyl-3-ethyl-4-methoxymethoxy-1-naphthyl)-2-oxo-acetate ethyl 2-(5-benzyl-4-methoxymethoxy-3-propyl-1-naphthyl)-2-oxo-acetate ethyl 2-(5-benzyl-3-butyl-4-methoxymethoxy-1-naphthyl)-2-oxo-acetate ethyl 2-(3-methoxy-1-methoxymethoxy-5-pentyl-1-naphthyl)-2-oxo-acetate.

REFERENTIAL EXAMPLE 22

Ethyl 2-(5-benzyl-4-methoxy-1-naphthyl)-2-oxo-acetate

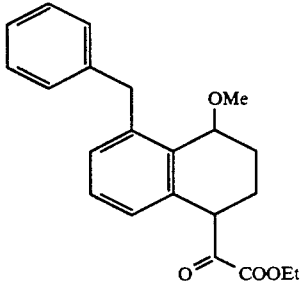

46.6 g of anhydrous aluminum chloride was suspended in 400 ml of dichloromethane and the obtained suspension was stirred under cooling with ice, followed by the dropwise addition of a solution of 49.6 g of 8-benzyl-1-methoxynaphthalene and 31.2 g of ethyloxalyl chloride in 500 ml of dichloromethane. After the completion of the dropwise addition, the obtained mixture was stirred under cooling with ice for 30 minutes and poured onto ice-water. The obtained mixture was extracted with ethyl acetate. The organic layer was washed with a saturated aqueous solution of sodium chloride twice, dried over anhydrous magnesium sulfate and distilled in a vacuum to remove the solvent. The obtained residue was purified by silica gel column chromatography (developer: 10 to 20% ethyl acetate/hexane) to give 44 g of the title compound as a yellow crystal.

$^1$H-NMR (400 MHz, CDCl$_3$) δ: 1.42 (t, J=7.2 Hz, 3H), 3.76 (s, 3H), 4.45 (q, J=7.2 Hz, 2H), 4.66 (s, 2H), 6.74 (d, J=8.0 Hz, 1H), 7.01 (d, J=8.0 Hz, 2H), 7.13 (t, J=8.0 Hz, 1H), 7.22 (t, J=8.0 Hz, 2H), 7.37 (d, J=8.0 Hz, 1H), 7.62 (t, J=8.0 Hz, 1H), 7.88 (d, J=8.0 Hz, 1H), 9.21 (d, J=8.0 Hz, 1H).

REFERENTIAL EXAMPLE 23

Ethyl 4-(5-benzyl-3-methoxy-4-methoxymethoxy-1-naphthyl)-4-oxo-butyrate

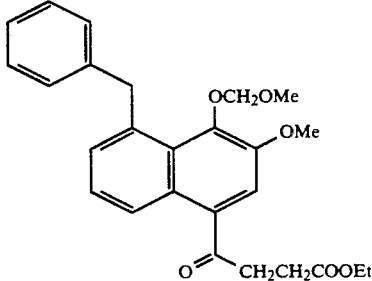

The title compound was prepared in a similar manner to that of the Referential Example 12 except that ethylsuccinyl chloride was used instead of the ethyloxalyl chloride.

REFERENTIAL EXAMPLE 24

Ethyl 3-(5-benzyl-3-methoxy-4-methoxymethoxy-1-naphthyl)-2, 2-dimethyl-3-oxo-propionate

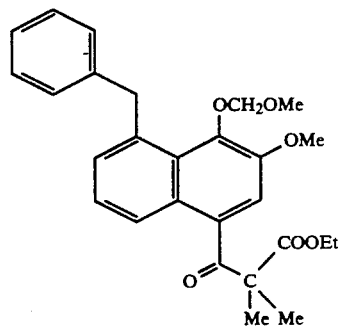

(a) synthesis of ethyl 3-(5-benzyl-4-hydroxy-3-methoxy-1-naphthyl)-3-oxo-propionate

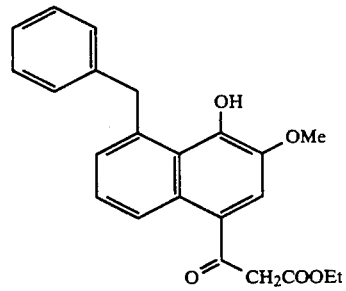

4.5 g of anhydrous aluminum chloride was suspended in 200 ml of dichloromethane. 3.6 ml of ethylmalonyl chloride was added to the suspension at room temperature. A solution of 5.0 g of 8-benzyl-2-methoxy-1-naphthol in 100 ml of dichloromethane was dropped into the obtained mixture under cooling with ice. The obtained mixture was stirred at room temperature for 8 hours and poured onto 1 l of ice-water. The organic layer was washed with water, dried over anhydrous magnesium sulfate and concentrated in a vacuum. The residue was purified by silica gel column chromatography (developer: 16% ethyl acetate/hexane) to give 2.64 g of the title compound as a deep-yellow oil.

(b) synthesis of ethyl 3-(5-benzyl-3-methoxy-4-methoxymethoxy-1-naphthyl)-3-oxo-propionate

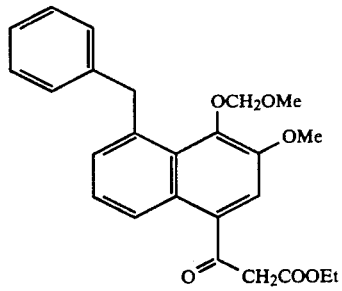

2.64 g of the naphthol prepared in the step (a) was dissolved in 50 ml of dichloromethane to give a solution. 1.8 ml of N,N-diisopropylethylamine and 0.7 ml of chloromethyl methyl ether were added to the solution successively. The obtained mixture was stirred at room temperature for 30 minutes, washed with dilute hydrochloric acid, water, a saturated aqueous solution of sodium hydrogencarbonate and water successively, dried over anhydrous magnesium sulfate and distilled in a vacuum to remove the solvent. The obtained residue was purified by silica gel column chromatography (developer: 10% ethyl acetate/hexane) to give 1.92 g of the title compound as a yellow oil.

(c) synthesis of ethyl 3-(5-benzyl-3-methoxy-4-methoxymethoxy-1-naphthyl)-2,2-dimethyl-3-oxo-propionate

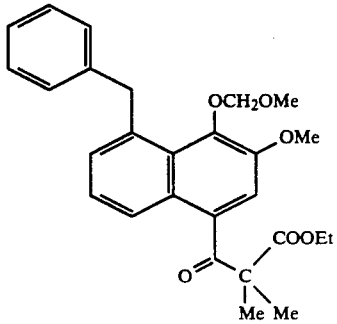

1.9 g of the methoxymethyl ether prepared in the step (b) was dissolved in 50 ml of N,N-dimethylformamide to give a solution. 0.44 g of sodium hydride (55% suspension in oil) was added to the solution at room temperature. The obtained mixture was stirred for 30 minutes, followed by the addition of 0.86 ml of methyl iodide. The obtained mixture was stirred for one hour and poured onto ice-water. The obtained mixture was extracted with ethyl acetate. The organic layer was washed with a saturated aqueous solution of sodium chloride, dried over anhydrous magnesium sulfate and concentrated in a vacuum. The obtained residue was purified by silica gel column chromatography (developer: 10% ethyl acetate/hexane) to give 1.47 g of the title compound as a yellow oil.

$^1$H-NMR (400 MHz, CDCl$_3$) δ: 0.96 (t, J=7.5 Hz, 3H), 1.58 (s, 6H), 3.43 (s, 3H), 3.88 (s, 3H), 4.04 (q, J=7.5 Hz, 2H), 4.80 (s, 2H), 5.10 (s, 2H), 7.06~7.14 (m, 8H), 7.78 (br d, J=8.5 Hz, 1H).

REFERENTIAL EXAMPLES 25 TO 28

The following compounds were each prepared in a similar manner to that described in the Referential Examples 1 and 12:

ethyl 2-[5-(p-chlorobenzyl)-3-methoxy-4-methoxymethoxy-1-naphthyl]-2-oxo-acetate ethyl 2-[3-methoxy-5-(p-methoxybenzyl)-4-methoxymethoxy-1-naphthyl]-2-oxo-acetate ethyl 2-[3-methoxy-4-methoxymethoxy-5-(p-methylbenzyl)-1-naphthyl]-2-oxo-acetate ethyl 2-[3-methoxy-5-(o-methoxybenzyl)-4-methoxymethoxy-1-naphthyl]-2-oxo-acetate.

REFERENTIAL EXAMPLE 29

2-(5-Benzyl-3-methoxy-4-methoxymethoxy-1-naphthyl)-2-oxo-acetic acid

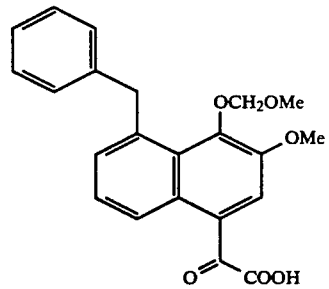

3 g of the ester prepared in the Referential Example 12 was suspended in 30 ml of ethanol, followed by the addition of 10 ml of water and 320 mg of sodium hydroxide. The obtained mixture was stirred at room temperature until the ester was dissolved completely, followed by the addition of a saturated aqueous solution of ammonium chloride. The pH of the mixture was adjusted to 5 by the addition of 1N hydrochloric acid. The resulting mixture was extracted with ethyl acetate under salting out. The organic layer was dried over anhydrous magnesium sulfate and filtered. The filtrate was distilled to remove the solvent. The obtained residue was used as such as a starting compound. The residue was recrystallized from ethyl acetate/hexane to give 2.34 g of the title compound as a pale yellow crystal.

m.p.: 75° to 79° C.

$^1$H-NMR (400 MHz, DMSO-d$_6$) δ: 3.35 (s, 3H), 3.83 (s, 3H), 4.71 (br s, 2H), 5.13 (s, 2H), 7.02 (br d, J=7.7 Hz, 2H), 7.09 (br t, J=7.7 Hz, 1H), 7.19 (br t, J=7.7 Hz, 2H), 7.21 (br s, 1H), 7.26 (dd, J=7.1 Hz, 1.2 Hz, 1H), 7.34 (dd, J=8.6 Hz, 7.1 Hz, 1H), 7.88 (s, 1H), 8.71 (dd, J=8.6 Hz, 1.2 Hz, 1H).

REFERENTIAL EXAMPLES 30 TO 41

The following compounds were prepared in a similar manner to that of the Referential Example 29 respectively from the compounds prepared in the Referential Examples 13 to 21 and 25 to 27:

2-(5-benzyl-3-ethoxy-4-methoxymethoxy-1-naphthyl)-2-oxo-acetic acid 2-(5-benzyl-4-methoxymethoxy-3-propoxy-1-naphthyl)-2-oxo-acetic acid 2-(5-benzyl-3-isopropoxy-4-methoxymethoxy-1-naphthyl)-2-oxo-acetic acid 2-(5-benzyl-3-cyclopentyloxy-4-methoxymethoxy-1-naphthyl)-2-oxo-acetic acid 2-(5-benzyl-4-methoxymethoxy-3-methyl-1-naphthyl)-2-oxo-acetic acid 2-(5-benzyl-3-ethyl-4-methoxymethoxy-1-naphthyl)-2-oxo-acetic acid 2-(5-benzyl-4-methoxymethoxy-3-propyl-1-naphthyl)-2-oxo-acetic acid 2-(5-benzyl-3-butyl-4-methoxymethoxy-1-naphthyl)-2-oxo-acetic acid 2-(3-methoxy-1-methoxymethoxy-5-pentyl-1-naphthyl)-2-oxo-acetic acid 2-[5-(p-chlorobenzyl)-3-methoxy-4-methoxymethoxy-1-naphthyl]-2-oxo-acetic acid 2-[3-methoxy-5-(p-methoxybenzyl)-4-methoxymethoxy-1-naphthyl]-2-oxo-acetic acid 2-[3-methoxy-4-methoxymethoxy-5-(p-methylbenzyl)-1-naphthyl]-2-oxo-acetic acid.

EXAMPLE 1

(Z)-2-(5-Benzyl-4-hydroxy-3-methoxy-1-naphthyl)-2-butenoic acid

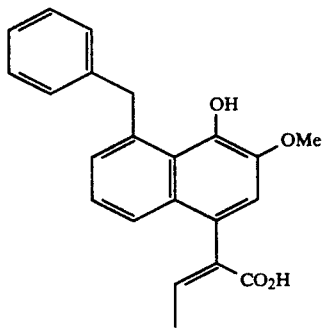

3.0 g of the ketocarboxylic acid prepared in the Referential Example 29 was dissolved in 50 ml of tetrahydrofuran to give a solution. 41 ml of a 1M solution of ethylmagnesium bromide in tetrahydrofuran was dropped into the solution in 5 minutes under cooling with ice. The obtained mixture was stirred for one hour under cooling with ice and poured onto ice-water. The obtained mixture was made weakly acidic with dilute hydrochloric acid and extracted with ethyl acetate. The organic layer was washed with water, dried over anhydrous magnesium sulfate and concentrated in a vacuum. 50 ml of 1,4-dioxane was added to the residue, followed by the dropwise addition of 0.5 ml of concentrated sulfuric acid at room temperature. The obtained mixture was refluxed under stirring for 30 minutes, cooled and poured onto ice-water. The obtained mixture was extracted with ethyl acetate. The organic layer was washed with water, dried over anhydrous magnesium sulfate and concentrated. 50 ml of benzene was added to the residue to precipitate a crystal. This crystal was recovered by filtration to give 1.0 g of the title compound as a pale-yellow crystal.

m.p.: 202° to 203° C.

$^1$H-NMR (400 MHz, CDCl$_3$) δ: 2.26 (d, J=7.2 Hz, 3H), 3.94 (s, 3H), 4.77 (s, 2H), 6.28 (br s, 1H), 6.43 (q, J=7.2 Hz, 1H), 7.11 (s, 1H), 7.11~7.27 (m, 7H), 7.61 (br d, J=8.4 Hz, 1H).

MS m/z (Pos, FAB): 348 (M+).

EXAMPLE 2

(Z)-2-(5-Benzyl-4-hydroxy-3-methoxy-1-naphthyl)-2-pentenoic acid

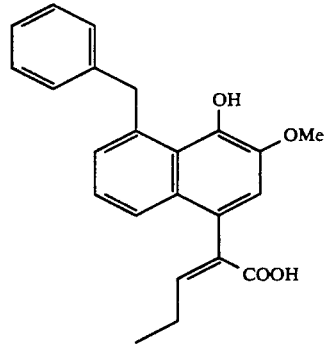

A part of a solution of 18.38 g of 1-bromopropane in 30 ml of tetrahydrofuran was added to a mixture comprising 3.63 g of magnesium, 40 ml of tetrahydrofuran and a catalytic amount of iodine. The obtained mixture was heated to initiate a reaction. The rest of the solution was dropped into the resulting mixture in 10 minutes and the obtained mixture was stirred at 80° C. for 30 minutes. Separately, 9.47 g of the carboxylic acid prepared in the Referential Example 29 was dissolved in 100 ml of tetrahydrofuran and the obtained solution was cooled with ice. The Grignard reagent prepared above was added to the solution in 10 minutes, followed by the addition of a saturated aqueous solution of ammonium chloride. The obtained mixture was extracted with ethyl acetate. The organic layer was dried over anhydrous magnesium sulfate and filtered. The filtrate was distilled to remove the solvent. The residue was dissolved in 100 ml of 1,4-dioxane, followed by the addition of 1.5 ml of concentrated sulfuric acid. The obtained mixture was stirred on an oil bath at 120° C. for 18 minutes and poured onto ice-water. The obtained mixture was extracted with ethyl acetate. The organic layer was washed with a saturated aqueous solution of sodium chloride twice, dried over anhydrous magnesium sulfate and filtered. The filtrate was distilled to remove the solvent. The residue was subjected to silica gel column chromatography (developer: 20% ethyl acetate/hexane). Diisopropyl ether was added to the obtained fraction to precipitate a crystal. This crystal was recovered by filtration and dissolved in 320 ml of ethanol, followed by the addition of 500 mg of Norit SX-3. The obtained mixture was stirred and filtered. The filtrate was concentrated and the precipitated crystal was recovered by filtration. 2.21 g of the title compound was obtained.

m.p.: 194° to 196° C.

$^1$H-NMR (400 MHz, CDCl$_3$) δ: 1.16 (t, J=7.5 Hz, 3H), 2.75 (quint, J=7.5 Hz, 2H), 3.95 (s, 3H), 4.77 (br s, 2H), 6.28 (br s, 1H), 6.31 (t, J=7.5 Hz, 1H), 7.11 (s, 1H), 7.1~7.3 (m, 7H), 7.62 (dd, J=8.4 Hz, 0.9 Hz, 1H).

MS m/z (Pos, FAB): 362 (M+).

EXAMPLE 3

(Z)-2-(5-Benzyl-4-hydroxy-3-methoxy-1-naphthyl)-2-hexenoic acid

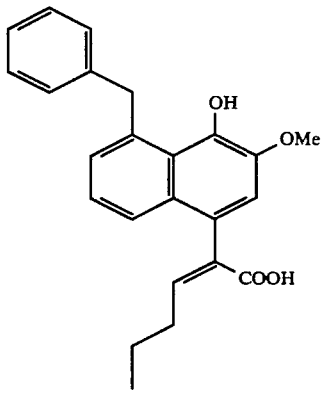

A part of a solution of 25.39 g of 1-bromobutane in 40 ml of tetrahydrofuran was added to a mixture comprising 4.5 g of magnesium, 40 ml of tetrahydrofuran and a catalytic amount of iodine. The obtained mixture was heated to initiate a reaction. The rest of the solution was dropped into the resulting mixture in 10 minutes and the obtained mixture was stirred at 80° C. for one hour. Separately, 11.75 g of the carboxylic acid prepared in the Referential Example 29 was dissolved in 100 ml of tetrahydrofuran and the obtained solution was cooled with ice. The Grignard reagent prepared above was added to the solution in 10 minutes, followed by the addition of ice-water and an aqueous solution of ammonium chloride. The obtained mixture was extracted with ethyl acetate under salting out and the organic layer was dried over anhydrous magnesium sulfate.

The resulting mixture was filtered and the filtrate was distilled in a vacuum to remove the solvent. The residue was dissolved in 120 ml of 1,4-dioxane, followed by the addition of 1.8 ml of concentrated sulfuric acid. The obtained mixture was stirred on an oil bath at 120° C. for 20 minutes and poured onto ice-water. The obtained mixture was extracted with ethyl acetate. The organic layer was washed with a saturated aqueous solution of sodium chloride twice, dried over anhydrous magnesium sulfate and filtered. The filtrate was distilled to remove the solvent. The residue was subjected to silica gel column chromatography (developer: 10 to 13% ethyl acetate/hexane). The obtained fraction was recrystallized from ethyl acetate/hexane. The obtained crystal was dissolved in 150 ml of ethanol, followed by the addition of 400 mg of Norit SX-3. The obtained mixture was stirred and filtered. The filtrate was concentrated to precipitate a crystal. This crystal was recovered by filtration to give 1.91 g of the title compound.

m.p.: 170° to 172° C.

$^1$H-NMR (400 MHz, CDCl$_3$)$\delta$: 1.00 (t, J=7.3 Hz, 3H), 1.57 (sixtet, J=7.3 Hz, 2H), 2.64 (q, J=7.3 Hz, 2H), 3.95 (s, 3H), 4.77 (s, 2H), 6.28 (br s, 1H), 6.32 (t, J=7.3 Hz, 1H), 7.11 (s, 1H), 7.1~7.28 (m, 7H), 7.62 (dd, J=8.5 Hz, 1.2 Hz, 1H).

MS m/z (Pos, FAB): 376 (M+).

EXAMPLE 4

(Z)-2-(5-Benzyl-4-hydroxy-3-methoxy-1-naphthyl)-4-methyl-2-pentenoic acid

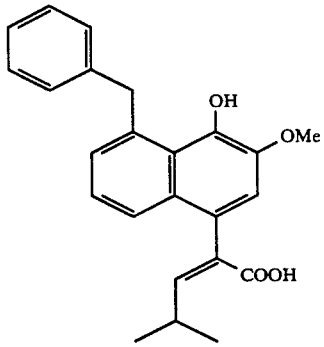

66.6 g of the carboxylic acid prepared in the Referential Example 29 was dissolved in 200 ml of tetrahydrofuran to give a solution. 300 ml of a 3M solution of isobutylmagnesium bromide in tetrahydrofuran was added to the solution under cooling with ice. The obtained mixture was stirred for 30 minutes and added to a saturated aqueous solution of ammonium chloride. The obtained mixture was extracted with ethyl acetate. The organic layer was washed with a saturated aqueous solution of sodium chloride, dried over anhydrous magnesium sulfate and distilled in a vacuum to remove the solvent. The residue was dissolved in 500 ml of 1,4-dioxane, followed by the addition of 5 ml of concentrated sulfuric acid. The obtained mixture was heated under reflux for 15 minutes and cooled to room temperature, followed by the addition of ethyl acetate. The obtained mixture was washed with water twice and with a saturated aqueous solution of sodium chloride thrice. The organic layer was dried over anhydrous magnesium sulfate and distilled in a vacuum to remove the solvent. The residue was purified by silica gel column chromatography (developer: 20% ethyl acetate/hexane) to give 9 g of the title compound as a pale-yellow crystal.

m.p.: 190° to 192° C.

$^1$H-NMR (400 MHz, CDCl$_3$)$\delta$: 1.14 (d, J=6.6 Hz, 6H), 3.43~3.60 (m, 1H), 3.96 (s, 3H), 4.77 (br s, 2H), 6.10 (d, J=10.1 Hz, 1H), 6.24 (br s, 1H), 7.10 (s, 1H), 7.10~7.28 (m, 7H), 7.62 (br d, J=8.6 Hz, 1H).

MS m/z (Pos, FAB): 376 (M+).

EXAMPLE 5

(Z)-2-(5-Benzyl-4-hydroxy-3-methoxy-1-naphthyl)-2,5-hexadienoic acid

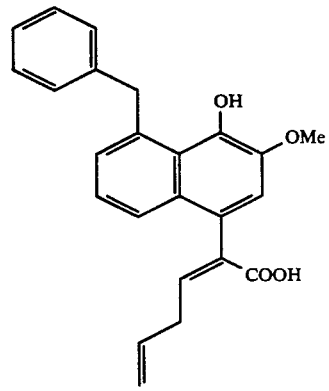

A part of a solution of 6.94 g of (bromomethyl)cyclopropane in 20 ml of tetrahydrofuran was added to a mixture comprising 1.25 g of magnesium, 20 ml of tetrahydrofuran and a catalytic amount of iodine. The obtained mixture was heated to initiate a reaction. The rest of the solution was dropped into the resulting mixture in 5 minutes. The obtained mixture was stirred at 80° C. for 30 minutes. Separately, 2.79 g of the carboxylic acid prepared in the Referential Example 29 was dissolved in 80 ml of tetrahydrofuran and the obtained solution was cooled with ice. The Grignard reagent prepared above was added to the solution, followed by the addition of a saturated aqueous solution of ammonium chloride. The obtained mixture was extracted with ethyl acetate. The organic layer was dried over anhydrous magnesium sulfate and filtered. The filtrate was distilled to remove the solvent. The residue was dissolved in 30 ml of 1,4-dioxane, followed by the addition of 0.9 ml of concentrated sulfuric acid. The obtained mixture was stirred on an oil bath at 120° C. for one hour and poured onto ice-water. The obtained mixture was extracted with ethyl acetate. The organic layer was washed with a saturated aqueous solution of sodium chloride twice, dried over anhydrous magnesium sulfate and filtered. The filtrate was distilled to remove the solvent. The residue was subjected to silica gel column chromatography (developer: 20% ethyl acetate/hexane). Diisopropyl ether was added to the obtained fraction. The obtained mixture was filtered to remove insolubles. The filtrate was distilled to remove the solvent. The residue was dissolved in diethylether, followed by the addition of hexane. The obtained mixture was cooled with ice to precipitate a crystal. This crystal was recovered by filtration and dissolved in 17 ml of ethanol, followed by the addition of 370 mg of Norit SX-3. The obtained mixture was stirred and filtered. The filtrate was distilled to remove the solvent. The residue was recrystallized from diethyl ether/hexane to give 220 mg of the title compound.

m.p.: 156° to 158° C.

¹H-NMR (400 MHz, CDCl₃)δ: 3.51 (br t, J=7.6 Hz, 2H), 3.95 (s, 3H), 5.10 (br d, J=10.0 Hz, 1H), 5.17 (br d, J=17.2 Hz, 1H), 5.88~6.00 (m, 1H), 6.30 (br s, 1H), 6.34 (t, J=7.6 Hz, 1H), 7.12 (s, 1H), 7.1~7.3 (m, 7H), 7.61 (br d, J=8.6 Hz, 1H).

MS m/z (Pos, FAB): 374 (M+).

EXAMPLE 6

(Z)-2-(5-Benzyl-4-hydroxy-3-methoxy-1-naphthyl)-6-methyl-2,5-heptadienoic acid

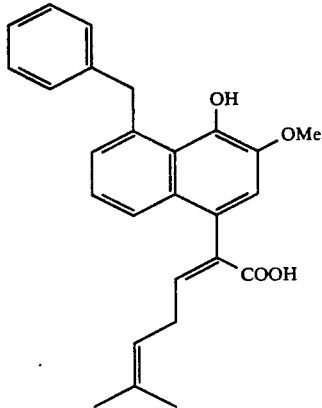

A part of a solution of 5 g of 5-bromo-2-methyl-2-pentene in 10 ml of tetrahydrofuran was added to a mixture comprising 750 mg of magnesium, 10 ml of tetrahydrofuran and a catalytic amount of iodine. The obtained mixture was heated to initiate a reaction. The rest of the solution was dropped into the resulting mixture in 10 minutes. The obtained mixture was stirred at 80° C. for 30 minutes. Separately, 2.33 g of the carboxylic acid prepared in the Referential Example 29 was dissolved in 60 ml of tetrahydrofuran and the obtained solution was cooled with ice. The Grignard reagent prepared above was added to the solution in 7 minutes, followed by the addition of a saturated aqueous solution of ammonium chloride. The obtained mixture was extracted with ethyl acetate. The organic layer was dried over anhydrous magnesium sulfate and filtered. The filtrate was distilled in a vacuum to remove the solvent. The residue was dissolved in 25 ml of 1,4-dioxane, followed by the addition of 0.45 ml of concentrated sulfuric acid. The obtained mixture was stirred on an oil bath at 120° C. for 30 minutes and poured onto ice-water. The obtained mixture was extracted with ethyl acetate. The organic layer was washed with a saturated aqueous solution of sodium chloride twice, dried over anhydrous magnesium sulfate and filtered. The filtrate was distilled to remove the solvent. The residue was subjected to silica gel column chromatography (developer: 10% ethyl acetate/hexane). Diisopropyl ether was added to the obtained fraction to precipitate a crystal. This crystal was recovered by filtration and dissolved in 25 ml of ethanol, followed by the addition of 60 mg of Norit SX-3. The obtained mixture was stirred and filtered. The filtrate was distilled to remove the solvent. The residue was recrystallized from diethylether/hexane to give 90 mg of the title compound.

m.p.: 154° to 156.5° C.

¹H-NMR (400 MHz, CDCl₃)δ: 1.69 (br s, 3H), 1.73 (br s, 3H), 3.46 (br t, J=7.5 Hz, 2H), 3.96 (s, 3H), 4.77 (br s, 2H), 5.2~5.3 (m, 1H), 6.26 (t, J=7.5 Hz, 1H), 6.2~6.35 (m, 1H), 7.12 (s, 1H), 7.1~7.3 (m, 7H), 7.62 (br d, J=8.6 Hz, 1H).

MS m/z (Pos, FAB): 402 (M+).

EXAMPLES 7 TO 39

The carboxylic acids prepared in the Referential Examples 30 to 41 were each reacted with a suitable Grignard reagent, and then obtained reaction mixtures were each treated in a similar manner to that of the Example 1 to give compounds listed in Table 2 as Examples 7 to 39.

TABLE 2

| Ex. No. | Objective compound structural formula and name | form | ¹H-NMR (400 MHz) δ, MS m/z | m.p. (°C.) |
|---|---|---|---|---|
| 7 | (Z)-2-(5-benzyl-4-hydroxy-3-methoxy-1-naphthyl)-2-heptenoic acid | light-brown crystal | 0.94 (t, J=7.5Hz, 3H), 1.41(sixtet, J=7.5Hz, 2H), 1.52(quint, J=7.5Hz, 2H), 2.74(t, J=7.5Hz, 2H), 3.94(s, 3H), 4.78 (s, 2H), 6.32(t, J=7.5Hz, 1H), 6.10~6.42(brs, 1H), 7.10~7.30(m, 8H), 7.62 (dd, J=7.5Hz, 1.3Hz, 1H) (CDCl₃) (Pos, FAB): 390 (M+) | 173 |

TABLE 2-continued

| Ex. No. | Objective compound structural formula and name | form | $^1$H-NMR (400 MHz) δ, MS m/z | m.p. (°C.) |
|---|---|---|---|---|
| 8 | 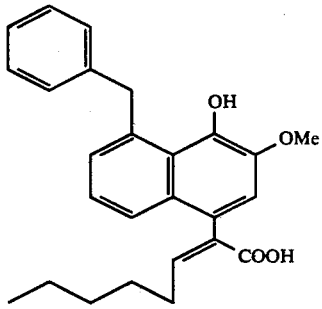(Z)-2-(5-benzyl-4-hydroxy-3-methoxy-1-naphthyl)-2-octenoic acid | pale-yellow crystal | 0.91(t, J=7.0Hz, 3H), 1.27~1.45(m, 4H), 1.46~1.60(m, 2H), 2.74(q, J=7.0Hz, 2H), 3.95(s, 3H), 4.77(s, 2H), 6.33(t, J=7.0Hz, 1H), 7.11(s, 1H), 7.08~7.32(m, 7H), 7.62(d, J=8.0Hz, 1H) (CDCl$_3$) (Pos, FAB): 404 (M$^+$) | 129~130 |
| 9 | 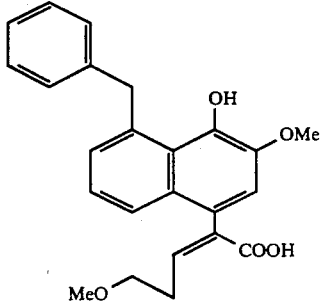(Z)-2-(5-benzyl-4-hydroxy-3-methoxy-1-naphthyl)-5-methoxy-2-pentenoic acid | light-brown crystal | 2.95(q, J=7.4Hz, 2H), 3.42(s, 3H), 3.60 (t, J=7.4Hz, 2H), 3.94(s, 3H), 4.78(s, 2H), 6.28(brs, 1H), 6.32(t, J=7.4Hz, 1H), 7.10~7.28(m, 8H), 7.60(brd, J=8.3Hz, 1H) (CDCl$_3$) | 138~141 |
| 10 | 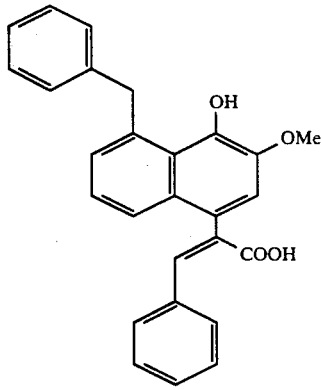(Z)-2-(5-benzyl-4-hydroxy-3-methoxy-1-naphthyl)-3-phenyl-2-propenoic acid | light-brown crystal | 3.96(s, 3H), 4.80(s, 2H), 6.36(brs, 1H), 7.04(s, 1H), 7.06~7.59(m, 12H), 7.88(brd, J=8.3Hz, 1H) (CDCl$_3$) | 135~138 |
| 11 | 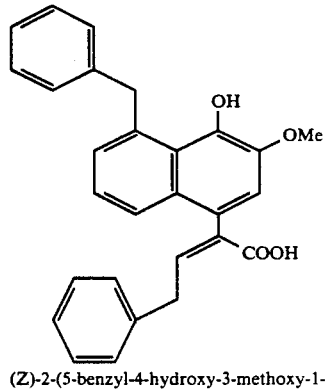(Z)-2-(5-benzyl-4-hydroxy-3-methoxy-1-naphthyl)-4-phenyl-2-butenoic acid | pale-yellow crystal | 3.94(s, 3H), 4.11(d, J=7.7Hz, 2H), 4.76 (brs, 2H), 6.29(brs, 1H), 6.48(brt, J=7.7Hz, 1H), 7.10~7.35(m, 13H), 7.64 (brd, J=8.8Hz, 1H) (CDCl$_3$) (Pos, FAB): 424 (M$^+$) | 179~182 |

TABLE 2-continued

| Ex. No. | Objective compound | | | m.p. (°C.) |
|---|---|---|---|---|
| | structural formula and name | form | ¹H-NMR (400 MHz) δ, MS m/z | |
| 12 | (Z)-2-(5-benzyl-4-hydroxy-3-methoxy-1-naphthyl)-3-cyclohexyl-2-propenoic acid | reddish purple crystal | 1.00~2.00(m, 10H), 3.10~3.30(m, 1H), 3.96(s, 3H), 4.78(brs, 2H), 6.12(d, J=10.1Hz, 1H), 6.29(brs, 1H), 7.10(s, 1H), 7.10~7.30(m, 7H), 7.63(brd, J=8.5Hz, 1H) (CDCl$_3$) (Pos, FAB): 416 (M$^+$) | 186.5~188.5 |
| 13 | (Z)-2-(5-benzyl-4-hydroxy-3-methoxy-1-naphthyl)-4,4-dimethyl-2-pentenoic acid | pale-yellow crystal | 1.29(s, 9H), 3.95(s, 3H), 4.76(s, 2H), 5.85(s, 1H), 6.28(brs, 1H), 7.05~7.30 (m, 8H), 7.89(d, J=8.4Hz, 1H) (CDCl$_3$) (Pos, FAB): 390 (M$^+$) | 163~164 |
| 14 | 2-(5-benzyl-4-hydroxy-3-methoxy-1-naphthyl)-2-propenoic acid | light-brown crystal | 3.92(s, 3H), 4.75(s, 2H), 5.96(s, 1H), 6.31(brs, 1H), 6.78(s, 1H), 7.06~7.18 (m, 8H), 7.52(brd, J=8.3Hz, 1H) (CDCl$_3$) | 191~194 |
| 15 | 2-(5-benzyl-4-hydroxy-3-methoxy-1-naphthyl)-3-methyl-2-butenoic acid | light-brown crystal | 1.56(s, 3H), 2.32(s, 3H), 3.92(s, 3H), 4.76(s, 2H), 6.28(brs, 1H), 7.04(s, 1H), 7.10~7.30(m, 7H), 7.56(brd, J=8.3Hz, 1H) (CDCl$_3$) | 168.5~169.0 |

TABLE 2-continued

| Ex. No. | Objective compound structural formula and name | form | $^1$H-NMR (400 MHz) δ, MS m/z | m.p. (°C.) |
|---|---|---|---|---|
| 16 | 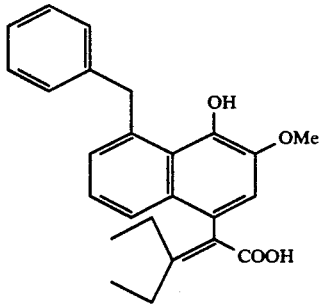<br>2-(5-benzyl-4-hydroxy-3-methoxy-1-naphthyl)-3-ethyl-2-pentenoic acid | purple crystal | 0.84(t, J=7.5Hz, 3H), 1.22(t, J=7.5Hz, 3H), 1.72~1.94(m, 2H), 2.50~2.62(m, 1H), 2.77~2.90(m, 1H), 3.94(s, 3H), 4.78(s, 2H), 6.28(brs, 1H), 7.04(s, 1H), 7.06~7.36(m, 7H), 7.58(brd, J=8.5Hz, 1H) (CDCl$_3$) | 188~189 |
| 17 | 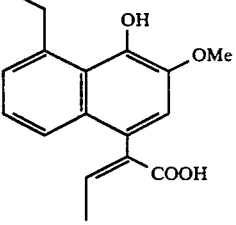<br>(Z)-2-[5-(p-chlorobenzyl)-4-hydroxy-3-methoxy-1-naphthyl]-2-propenoic acid | pale-purple crystal | 2.26(d, J=7.2Hz, 3H), 3.94(s, 3H), 4.70 (s, 2H), 6.24(brs, 1H), 6.46(q, J=7.2Hz, 1H), 7.04~7.28(m, 7H), 7.60(brd, J=8.5Hz, 1H) (CDCl$_3$) | 176.5~177 |
| 18 | 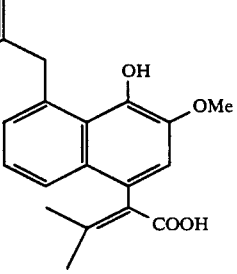<br>2-[5-(p-chlorobenzyl)-4-hydroxy-3-methoxy-1-naphthyl]-3-methyl-2-butenoic acid | pale-red crystal | 1.56(s, 3H), 2.32(s, 3H), 3.92(s, 3H), 4.70(s, 2H), 6.25(brs, 1H), 7.04(s, 1H), 7.06~7.28(m, 6H), 7.56(brd, J=8.3Hz, 1H) (CDCl$_3$) | 176.5 |
| 19 | 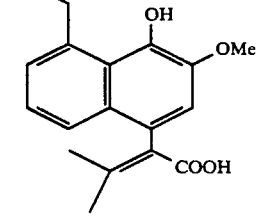<br>2-[4-hydroxy-5-(p-methoxybenzyl)-3-methoxy-1-naphthyl]-3-methyl-2-butenoic acid | pale-red crystal | 1.58(s, 3H), 2.35(s, 3H), 3.76(s, 3H), 3.94(s, 3H), 4.71(s, 2H), 6.30(s, 1H), 6.80(d, J=7.0Hz, 2H), 7.02~7.28(m, 5H), 7.54(brd, J=8.4Hz, 1H) (CDCl$_3$) | 143.0 |

TABLE 2-continued

| Ex. No. | Objective compound | | | m.p. (°C.) |
|---|---|---|---|---|
| | structural formula and name | form | $^1$H-NMR (400 MHz) δ, MS m/z | |
| 20 | 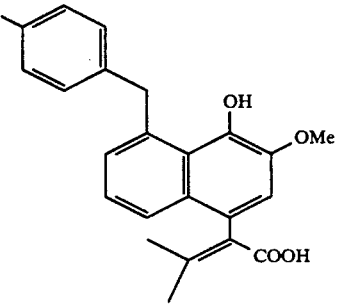<br>2-[4-hydroxy-3-methoxy-5-(p-methyl-benzyl)-1-naphthyl]-3-methyl-2-butenoic acid | pale-purple crystal | 1.56(s, 3H), 2.30(s, 3H), 2.34(s, 3H), 3.92(s, 3H), 4.74(s, 2H), 6.28(s, 1H), 7.00~7.14(m, 5H), 7.20(brt, J=8.3Hz, 1H), 7.26(s, 1H), 7.54(brd, J=8.3Hz, 1H) (CDCl$_3$) | 162.5~163.0 |
| 21 | 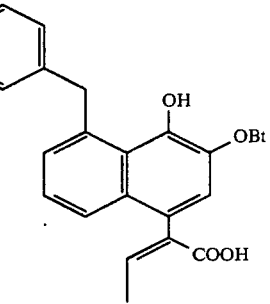<br>(Z)-2-[5-benzyl-3-ethoxy-4-hydroxy-1-naphthyl)-2-butenoic acid | gray crystal | 1.42(t, J=7.0Hz, 3H), 2.28(d, J=7.3Hz, 3H), 4.18(q, J=7.0Hz, 2H), 4.78(s, 2H), 6.36(s, 1H), 6.42(q, J=7.3Hz, 1H), 7.00~7.32(m, 8H), 7.60(d, J=8.3Hz, 1H) | 166~168 |
| 22 | 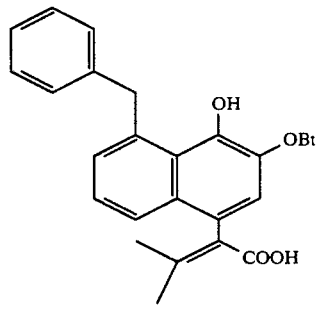<br>2-(5-benzyl-3-ethoxy-4-hydroxy-1-naphthyl)-3-methyl-2-butenoic acid | bluish-purple crystal | 1.44(t, J=7.0Hz, 3H), 1.60(s, 3H), 2.36 (s, 3H), 4.18(q, J=7.0Hz, 2H), 4.80(s, 2H), 6.36(brs, 1H), 6.98~7.36(m, 8H), 7.56(brd, J=8.5Hz, 1H) (CDCl$_3$) | 173~175 |
| 23 | 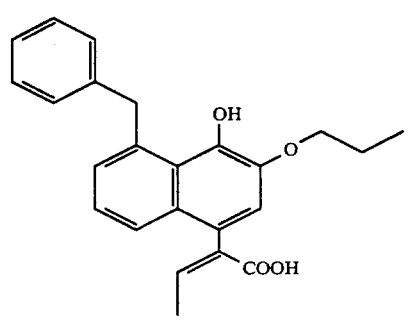<br>(Z)-2-(5-benzyl-4-hydroxy-3-propyloxy-1-naphthyl)-2-butenoic acid | gray crystal | 1.04(t, J=7.0Hz, 3H), 1.76~1.90(m, 2H), 2.26(d, J=7.2Hz, 3H), 4.06(t, J=7.0Hz, 2H), 4.78(s, 2H), 6.34(s, 1H), 6.42(q, J=7.2Hz, 1H), 7.00~7.30(m, 8H), 7.60 (brd, J=8.4Hz, 1H) (CDCl$_3$) | 195~197 |

TABLE 2-continued

| Ex. No. | Objective compound structural formula and name | form | $^1$H-NMR (400 MHz) δ, MS m/z | m.p. (°C.) |
|---|---|---|---|---|
| 24 | 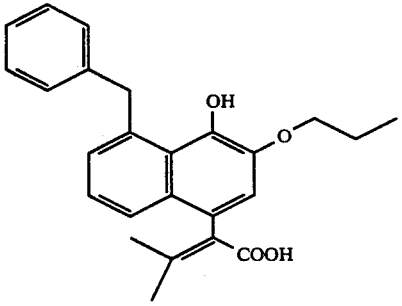<br>2-(5-benzyl-4-hydroxy-3-propyloxy-1-naphthyl)-3-methyl-2-butenoic acid | bluish-purple crystal | 1.04(t, J=7.0Hz, 3H), 1.56(s, 3H), 1.78~1.88(m, 2H), 2.33(s, 3H), 4.05(t, J=7.0Hz, 2H), 4.78(s, 2H), 6.35(brs, 1H), 7.03(s, 1H), 7.06~7.30(m, 7H), 7.56 (brd, J=8.4Hz, 1H) (CDCl$_3$) | 173~175 |
| 25 | 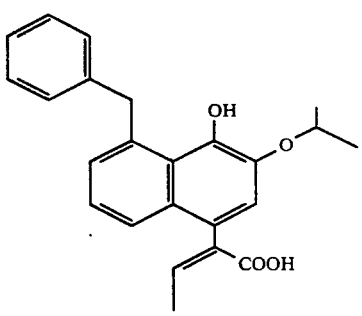<br>(Z)-2-(5-benzyl-4-hydroxy-3-isopropyloxy-1-naphthyl)-2-butenoic acid | pale-yellow crystal | 1.36(d, J=6.8Hz, 6H), 2.26(d, J=7.3Hz, 3H), 4.56~4.64(m, 1H), 4.78(s, 2H), 6.42(s, 1H), 6.43(q, J=7.3Hz, 1H), 7.02~7.28(m, 8H), 7.60(brd, J=8.3Hz, 1H) | 181~183 |
| 26 | 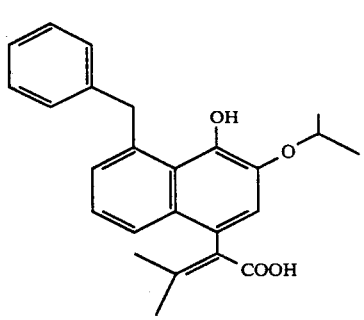<br>2-(5-benzyl-4-hydroxy-3-isopropyloxy-1-naphthyl)-3-methyl-2-butenoic acid | brown crystal | 1.34(d, J=6.8Hz, 6H), 1.56(s, 3H), 2.30 (s, 3H), 4.52~4.62(m, 1H), 4.78(s, 2H), 6.40(brs, 1H), 7.02(s, 1H), 7.06~7.30 (m, 7H), 7.56(brd, J=8.3Hz, 1H) (CDCl$_3$) | 212~214 |
| 27 | 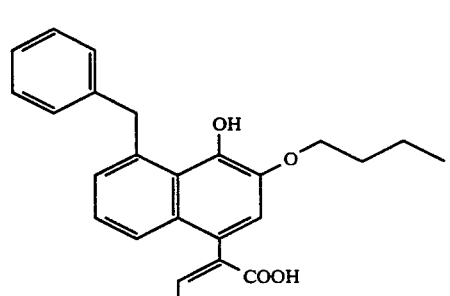<br>(Z)-2-(5-benzyl-3-butyloxy-4-hydroxy-1-naphthyl)-2-butenoic acid | bluish-purple crystal | 0.98(t, J=7.3Hz, 3H), 1.42~1.56(m, 2H), 1.72~1.84(m, 2H), 2.26(d, J=7.2Hz, 3H), 4.11(t, J=7.3Hz, 2H), 4.78(s, 2H), 6.34 (s, 1H), 6.42(q, J=7.2Hz, 1H), 7.02~7.30 (m, 8H), 7.60(brd, J=8.4Hz, 1H) (CDCl$_3$) | 196~198 |

TABLE 2-continued

| Ex. No. | Objective compound structural formula and name | form | $^1$H-NMR (400 MHz) δ, MS m/z | m.p. (°C.) |
|---|---|---|---|---|
| 28 | 2-(5-benzyl-3-butyloxy-4-hydroxy-1-naphthyl)-3-methyl-2-butenoic acid | bluish-purple crystal | 0.98(t, J=7.2Hz, 3H) 1.42~1.58(m, 2H), 1.58(s, 3H), 1.72~1.84(m, 2H), 2.34(s, 3H), 4.10(t, J=7.2Hz, 2H), 4.78(s, 2H), 6.34(s, 1H), 7.00~7.32(m, 8H), 7.56 (brd, J=8.5Hz, 1H) (CDCl$_3$) | 182~184 |
| 29 | (Z)-2-(5-benzyl-3-cyclopentyloxy-4-hydroxy-1-naphthyl)-2-butenoic acid | gray crystal | 1.60~1.98(m, 8H), 2.28(d, J=7.2Hz, 3H), 4.76(s, 2H), 4.86~4.94(m, 1H), 6.32(s, 1H), 6.45(q, J=7.2Hz, 1H), 7.04~7.36(m, 8H), 7.60(brd, J=8.4Hz, 1H) (CDCl$_3$) | 200~201 |
| 30 | 2-(5-benzyl-3-cyclopentyloxy-4-hydroxy-1-naphthyl)-3-methyl-2-butenoic acid | bluish-purple crystal | 1.56(s, 3H), 1.60~1.94(m, 8H), 2.32(s, 3H), 4.76(s, 2H), 4.84~4.90(m, 1H), 6.32(s, 1H), 7.04(s, 1H), 7.08~7.36(m, 7H), 7.54(d, J=8.0Hz, 1H) (CDCl$_3$) | 211~213 |
| 31 | (Z)-2-(5-benzyl-3-cyclopentyloxy-4-hydroxy-1-naphthyl)-2-pentenoic acid | light-blown crystal | 1.15(t, J=7.5Hz, 3H), 1.60~1.96(m, 8H), 2.75(quint, J=7.5Hz, 2H), 4.76(s, 2H), 4.86~4.92(m, 1H), 6.30(t, J=7.5Hz, 1H), 6.32(s, 1H), 7.08~7.30(m, 8H), 7.60 (dd, J=8.5Hz, 0.9Hz, 1H) (CDCl$_3$) | 191~193 |

TABLE 2-continued

| Ex. No. | Objective compound structural formula and name | form | $^1$H-NMR (400 MHz) δ, MS m/z | m.p. (°C.) |
|---|---|---|---|---|
| 32 | 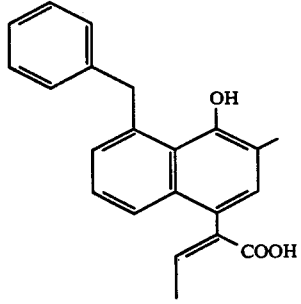<br>(Z)-2-(5-benzyl-4-hydroxy-3-methyl-1-naphthyl]-2-butenoic acid | colorless crystal | 2.26(d, J=7.0Hz, 3H), 2.28(s, 3H), 4.73 (s, 2H), 6.36(q, J=7.0Hz, 1H), 7.12(s, 1H), 7.05~7.30(m, 6H), 7.32(t, J=8.0Hz, 1H), 7.68(d, J=8.0Hz, 1H) (CDCl$_3$)<br>(Pos, FAB): 332 (M$^+$) | 173~175 |
| 33 | 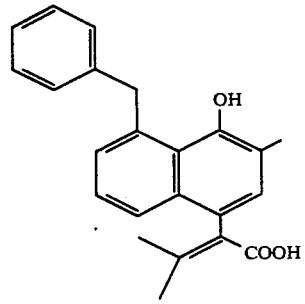<br>2-(5-benzyl-4-hydroxy-3-methyl-1-naphthyl)-3-methyl-2-butenoic acid | pale-yellow crystal | 1.57(s, 3H), 2.29(s, 3H), 2.33(s, 3H), 4.73(d, J=20Hz, 1H), 4.77(d, J=20Hz, 1H), 7.07(s, 1H), 7.12~7.35(m, 7H), 7.65(d, J=8.0Hz, 1H) (CDCl$_3$)<br>(Pos, FAB): 346 (M$^+$) | 202~204 |
| 34 | 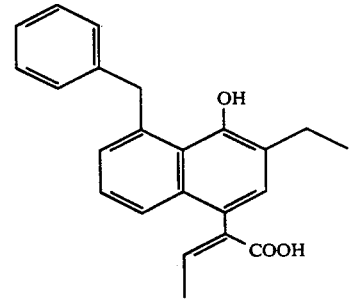<br>(Z)-2-(5-benzyl-3-ethyl-4-hydroxy-1-naphthyl)-2-butenoic acid | colorless crystal | 1.24(t, J=7.0Hz, 3H), 2.26(d, J=7.0Hz, 3H), 2.66(q, J=7.0Hz, 2H), 4.76(s, 2H), 6.34(q, J=7.0Hz, 1H), 7.05~7.37(m, 8H), 7.70(d, J=8.0Hz, 1H) (CDCl$_3$)<br>(Pos, FAB): 346 (M$^+$) | 193~195 |
| 35 | 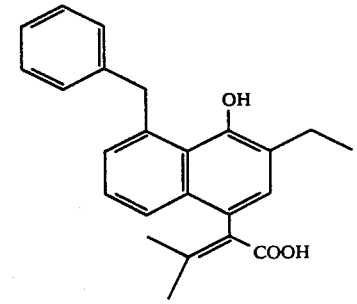<br>2-(5-benzyl-3-ethyl-4-hydroxy-1-naphthyl)-3-methyl-2-butenoic acid | colorless crystal | 1.25(t, J=7.0Hz, 3H), 1.58(s, 3H), 2.35 (s, 3H), 2.66(q, J=7.0Hz, 2H), 4.73(d, J=20Hz, 1H), 4.77(d, J=20Hz, 1H), 7.09(s, 1H), 7.12~7.36(m, 7H), 7.65(d, J=8.0Hz, 1H) (CDCl$_3$)<br>(Pos, FAB): 360 (M$^+$) | 166~168 |

TABLE 2-continued

| Ex. No. | Objective compound structural formula and name | form | $^1$H-NMR (400 MHz) δ, MS m/z | m.p. (°C.) |
|---|---|---|---|---|
| 36 | 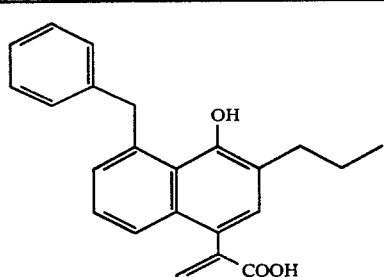<br>(Z)-2-(5-benzyl-4-hydroxy-3-propyl-1-naphthyl)-2-butenoic acid | colorless crystal | 0.97(t, J=7.0Hz, 3H), 1.55~1.72(m, 2H), 2.27(d, J=7.0Hz, 3H), 2.60(t, J=7.0Hz, 2H), 4.75(s, 2H), 6.37(q, J=7.0Hz, 1H), 7.12(s, 1H), 7.10~7.32(m, 6H), 7.33(t, J=8.0Hz, 1H), 7.68(d, J=8.0Hz, 1H) (CDCl$_3$) (Pos, FAB): 360 (M$^+$) | 164~167 |
| 37 | 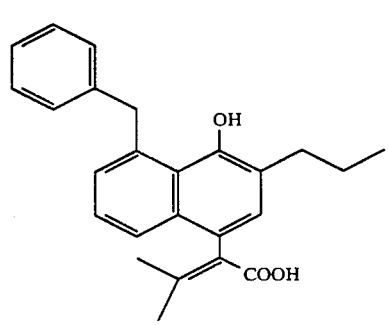<br>2-(5-benzyl-4-hydroxy-3-propyl-1-naphthyl)-3-methyl-2-butenoic acid | colorless crystal | 0.95(t, J=7.0Hz, 3H), 1.58(s, 3H), 1.45~1.67(m, 2H), 2.34(s, 3H), 2.52~2.70(m, 2H), 4.70(d, J=20Hz, 1H), 4.78(d, J=20Hz, 1H), 5.12(brs, 1H), 7.04(s, 1H), 7.10~7.34(m, 7H), 7.62(d, J=8.0Hz, 1H) (CDCl$_3$) (Pos, FAB): 3.74 (M$^+$) | 163~165 |
| 38 | 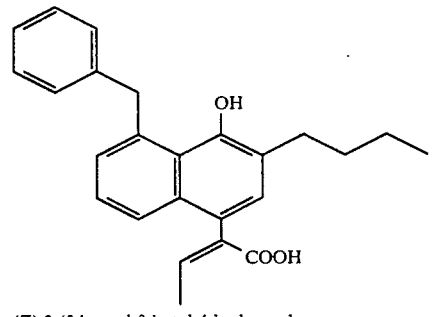<br>(Z)-2-(5-benzyl-3-butyl-4-hydroxy-1-naphthyl)-2-butenoic acid | colorless crystal | 0.91(t, J=7.0Hz, 3H), 1.30~1.45(m, 2H), 1.51~1.70(m, 2H), 2.16(d, J=7.0Hz, 3H), 2.62(t, J=7.0Hz, 2H), 4.75(s, 2H), 6.36 (q, J=7.0Hz, 1H), 7.12(s, 1H), 7.10~7.32 (m, 6H), 7.33(t, J=8.0Hz, 1H), 7.69(d, J=8.0Hz, 1H) (CDCl$_3$) (Pos, FAB): 374 (M$^+$) | 174~176 |
| 39 | 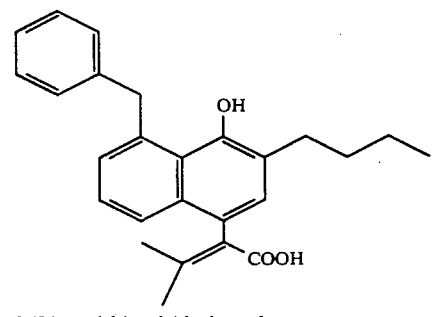<br>2-(5-benzyl-3-butyl-4-hydroxy-1-naphthyl)-3-methyl-2-butenoic acid | pale-yellow crystal | 0.92(t, J=7.0Hz, 3H), 1.28~1.44(m, 2H), 1.45~1.72(m, 2H), 1.59(s, 3H), 2.36(s, 3H), 2.62(t, J=7.0Hz, 2H), 4.71(d, J=16Hz, 1H), 4.78(d, J=16Hz, 1H), 5.09(s, 1H), 7.05(s, 1H), 7.08~7.47(m, 7H), 7.62(d, J=8.0Hz, 1H) (CDCl$_3$) | 194~196 |

EXAMPLE 40

(E)-2-(5-Benzyl-4-hydroxy-3-methoxy-1-naphthyl)-2-butenoic acid

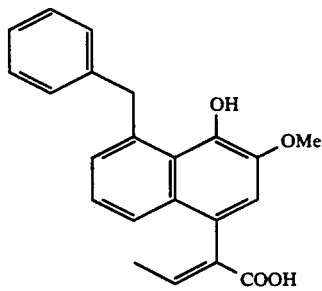

(a) synthesis of ethyl (E)-2-(5-benzyl-3-methoxy-4-methoxymethoxy-1-naphthyl)-2-butenoate

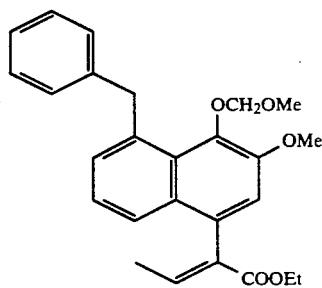

2.78 g of ethyltriphenylphosphonium bromide was suspended in 20 ml of tetrahydrofuran to give a suspension. 3.0 ml of a 2.5M solution of n-butyllithium in hexane was dropped into the suspension in a stream of nitrogen at −70° C. in 5 minutes. The temperature of the resulting mixture was raised to 0° C. The resulting mixture was stirred for 30 minutes. A solution of 1.98 g of the ketoester prepared in the Referential Example 12 in 10 ml of tetrahydrofuran was added to the mixture in 5 minutes. The obtained mixture was stirred at 0° C. for 30 minutes and at room temperature for 2 hours, followed by the addition of 20 ml of an aqueous solution of ammonium chloride. The obtained mixture was stirred for 2 hours and extracted with ether. The organic layer was washed with water, dried over anhydrous magnesium sulfate and purified by silica gel column chromatography (developer: 5% ethyl acetate/hexane) to give 1.2 g of the title compound as a colorless oil.

(b) synthesis of (E)-2-(5-benzyl-4-hydroxy-3-methoxy-1-naphthyl)-2-butenoic acid

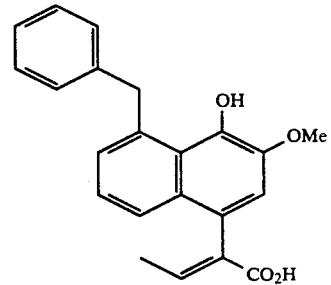

1.2 g of the ester prepared in the step (a) was dissolved in 50 ml of ethanol, followed by the addition of 10 ml of water and 3 g of sodium hydroxide. The obtained mixture was stirred at 80° C. for 30 minutes, cooled and poured onto ice-water. The obtained mixture was made weakly acidic with dilute hydrochloric acid and extracted with ethyl acetate. The organic layer was washed with water, dried over anhydrous magnesium sulfate and concentrated. 20 ml of acetone and 20 ml of 6N hydrochloric acid were added to the residue. The obtained mixture was stirred at room temperature for 2 hours, followed by the addition of 100 ml of a saturated aqueous solution of sodium chloride. The obtained mixture was extracted with ethyl acetate. The organic layer was washed with water, dried over anhydrous magnesium sulfate and concentrated. The residue was recrystallized from diisopropylether to give 350 mg of the title compound as a colorless crystal.

m.p.: 190° to 192° C.

$^1$H-NMR (400 MHz, CDCl$_3$) δ: 1.61 (d, J=7.2 Hz, 3H), 3.92 (s, 3H), 4.87 (s, 2H), 6.30 (br s, 1H), 7.02 (s, 1H), 7.08~7.26 (m, 7H), 7.42~7.56 (m, 2H).

MS m/z (Pos, FAB): 348 (M+).

EXAMPLE 41

3-(5-Benzyl-4-hydroxy-3-methoxy-1-naphthyl)-2, 2-dimethyl-3-butenoic acid

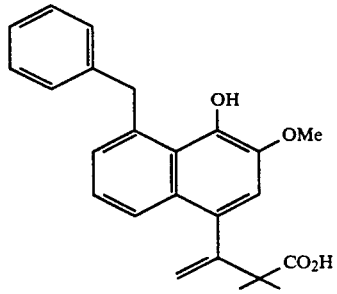

(a) synthesis of ethyl 3-(5-benzyl-3-methoxy-4-methoxymethoxy-1-naphthyl)-2.2-dimethyl-3-butenoate

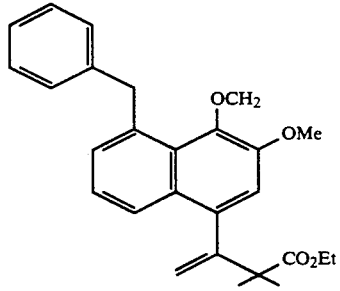

1.47 g of the ketoester prepared in the Referential Example 24 was dissolved in 50 ml of 1,2-dimethoxyethane, followed by the addition of 0.17 g of sodium hydride (55% suspension in oil) and 1.51 g of methyltriphenylphosphonium bromide. The obtained mixture was heated under reflux for 2 hours and cooled by allowing to stand, followed by the addition of ethyl acetate. The obtained mixture was washed with water and the organic layer was dried over anhydrous magnesium sulfate and concentrated in a vacuum. The residue was purified by silica gel column chromatography (developer: 5% ethyl acetate/hexane) to give 700 mg of the title compound as a colorless oil.

$^1$H-NMR (400 MHz, CDCl$_3$) δ: 1.18 (t, J=7.3 Hz, 3H), 1.30 (br s, 3H), 1.42 (br s, 3H), 3.50 (s, 3H), 3.92 (s, 3H), 4.08 (q, J=7.3 Hz, 2H), 4.81 (br s, 2H), 5.08 (s, 2H), 5.20 (s, 1H), 5.67 (s, 1H), 7.04 (s, 1H), 7.08~7.36 (m, 7H), 7.84 (br d, J=8.3 Hz, 1H).

(b) synthesis of 3-(5-benzyl-3-methoxy-4-nethoxymethoxy-1-naphthyl)-2,2-dimethyl-3-butenoic acid

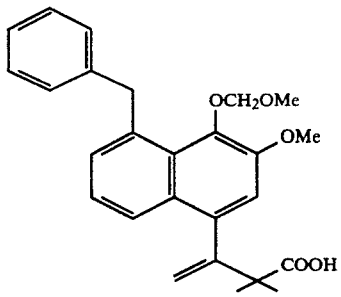

700 mg of the ethyl 3-butenoate prepared in the step (a) was suspended in ethanol/water (30 ml/10 ml), followed by the addition of 200 mg of potassium hydroxide. The obtained mixture was heated under reflux for 6 hours and cooled by allowing to stand, followed by the addition of water. The obtained mixture was acidified with dilute hydrochloric acid and extracted with ethyl acetate. The organic layer was washed with water, dried over anhydrous magnesium sulfate and concentrated in a vacuum. The obtained residue was used in the subsequent step without being purified.

(c) synthesis of 3-(5-benzyl-4-hydroxy-3-methoxy-1-naphthyl)-2.2-dimethyl-3-butenoic acid

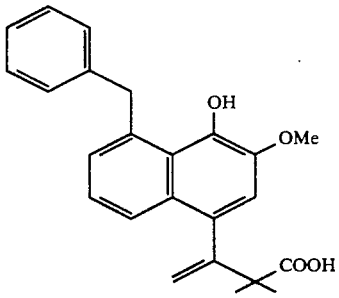

The carboxylic acid prepared in the step (b) was dissolved in 5 ml of acetone, followed by the addition of 2 ml of 6N hydrochloric acid. The obtained mixture was stirred at room temperature for one hour, followed by the addition of ethyl acetate. The organic layer was washed with water, dried over anhydrous magnesium sulfate and distilled in a vacuum to remove the solvent. The obtained solid was washed with diisopropylether to give 300 mg of the title compound as a colorless crystal.

m.p.: 162.5° C.

$^1$H-NMR (400 MHz, CDCl$_3$) δ: 1.24 (br s, 3H), 1.46 (br s, 3H), 3.78 (s, 3H), 4.78 (s, 2H), 5.24 (s, 1H), 5.72 (s, 1H), 6.18 (s, 1H), 7.06 (s, 1H), 7.08~7.30 (m, 7H), 7.82 (br d, J=8.2 Hz, 1H).

EXAMPLE 42

(E)-2-(5-Benzyl-4-hydroxy-3-methoxy-1-naphthyl)-3-cyano-2-propenoic acid

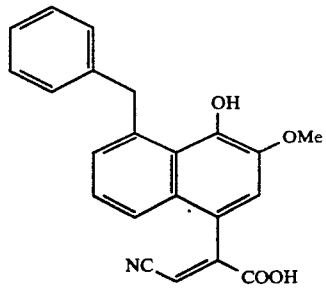

(a) synthesis of ethyl 2-(5-benzyl-3-methoxy-4-methoxymethoxy-1-naphthyl)-3-cyano-2-propenoate

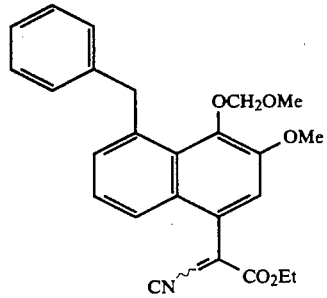

1.72 g of diethyl cyanomethylphosphonate was dissolved in 50 ml of N,N-dimethylformamide, followed by the addition of 0.44 g of sodium hydride (55% suspension in oil). A solution of 3.56 g of the ketoester prepared in the Referential Example 12 in 10 ml of N,N-dimethylformamide was dropped into the mixture under cooling with ice. After the completion of the reaction, the reaction mixture was poured onto water-ethyl acetate. The obtained mixture was washed with water twice. The organic layer was dried over anhydrous sodium sulfate and distilled in a vacuum to remove the solvent. The obtained residue was purified by silica gel column chromatography (developer: 10% ethyl acetate/hexane) to give 3.59 g of the title compound as a reddish-brown oil.

(b) synthesis of (E)-2-(5-benzyl-3-methoxy-4-methoxymethoxy-1-naphthyl)-3-cyano-2-propenoic acid

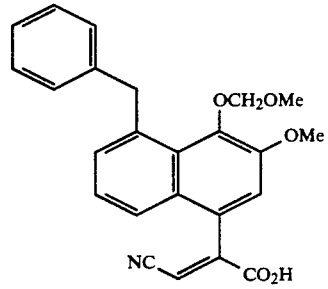

0.79 g of the cyano derivative prepared in the step (a) was dissolved in methanol/water (45 ml/5 ml), followed by the addition of 0.8 ml of 8N sodium hydroxide. The obtained mixture was stirred at room temperature. After the completion of the reaction, the reaction mixture was neutralized with 1N hydrochloric acid and extracted with ethyl acetate under salting out. The organic layer was dried over anhydrous sodium sulfate and distilled in a vacuum to remove the solvent.

¹H-NMR (400 MHz, CDCl₃) δ: 3.48 (s, 3H), 3.9 (s, 3H), 4.8 (s, 2H), 5.12 (s, 2H), 4.76 (s, 1H), 7.0~7.34 (m, 10H).

(c) synthesis of (E)-2-(5-benzyl-4-hydroxy-3-methoxy-1-naphthyl)-3-cyano-2-propenoic acid

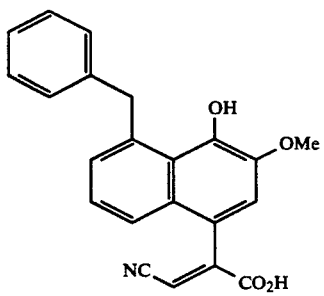

0.80 g of the carboxylic acid prepared in the step (b) was dissolved in 15 ml of acetone, followed by the addition of 0.5 ml of concentrated hydrochloric acid. The obtained mixture was stirred at room temperature. After the completion of the reaction, the reaction mixture was poured into water and the obtained mixture was extracted with ethyl acetate. The organic layer was dried over anhydrous sodium sulfate and distilled in a vacuum to remove the solvent. The obtained residue was purified by silica gel column chromatography (developer: 0 to 10% methanol/dichloromethane) to give 0.35 g of the title compound as a pale-yellow powder.

m.p.: 175° C. (dec.).

¹H-NMR (400 MHz, DMSO-d₆) δ: 3.85 (s, 3H), 4.72 (s, 2H), 6.78 (s, 1H), 7.0~7.25 (m, 8H), 7.3 (s, 1H), 7.37 (s, 1H), 9.25 (s, 1H).

MS m/z (Pos, FAB): 359 (M+).

EXAMPLE 43 TO 52

The ketoesters prepared in the Referential Examples 12 to 21, 23 and 28 were each reacted with a suitable Wittig reagent, and then the reaction mixtures were each treated in a similar manner to that of the Example 40 to give compounds listed in Table 3 as Examples 43 to 52.

TABLE 3

| Ex. No. | Objective compound structural formula and name | form | ¹H-NMR (400 MHz) δ, MS m/z | m.p. (°C.) |
|---|---|---|---|---|
| 43 | (E)-2-(5-benzyl-4-hydroxy-3-methoxy-1-naphthyl)-2-pentenoic acid | pale-yellow crystal | 0.95(t, J=7.5Hz, 3H), 1.94(quint, J=7.5Hz, 2H), 3.92(s, 3H), 4.76(s, 2H), 6.30(brs, 1H), 7.00(s, 1H), 7.08~7.18 (m, 7H), 7.38(t, J=7.5Hz, 1H), 7.46(brd, J=8.4Hz, 1H) (CDCl₃) | 187~188 |
| 44 | (E)-2-(5-benzyl-4-hydroxy-3-methoxy-1-naphthyl)-2-hexenoic acid | pale-yellow crystal | 0.82(t, J=7.3Hz, 3H), 1.40(sixtet, J=7.3Hz, 2H), 1.90(q, J=7.3Hz, 2H), 3.92 (s, 3H), 4.77(s, 2H), 6.30(brs, 1H), 7.00 (s, 1H), 7.10~7.28(m, 7H), 7.40(t, J=7.3Hz, 1H), 7.46(brd, J=8.3Hz, 1H) (CDCl₃) | 168~169 |
| 45 | (E)-2-(5-benzyl-4-hydroxy-3-methoxy-1-naphthyl)-2-heptenoic acid | pale-yellow crystal | 0.78(t, J=7.7Hz, 3H), 1.22(sixtet, J=7.7Hz, 2H), 1.37(quint, J=7.7Hz, 2H), 1.93(dt, J=7.5Hz, 7.7Hz, 2H), 3.92(s, 3H), 4.79(s, 2H), 6.31(brs, 1H), 7.01(s, 1H), 7.12~7.27(m, 8H), 7.41(t, J=7.5Hz, 1H, 7.48(dd, J=8.4Hz, 1.3Hz, 1H) (CDCl₃) (Pos, FAB): 390 (M+) | 134 |

TABLE 3-continued

| Ex. No. | Objective compound structural formula and name | form | $^1$H-NMR (400 MHz) δ, MS m/z | m.p. (°C.) |
|---|---|---|---|---|
| 46 | 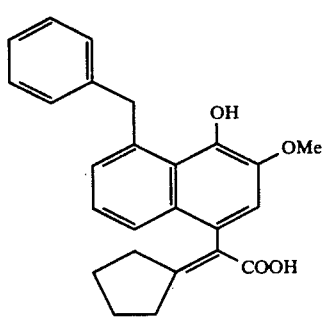<br>2-(5-benzyl-4-hydroxy-3-methoxy-1-naphthyl)-2-cyclopentylidene-ethanoic acid | colorless crystal | 1.42~2.18(m, 6H), 2.92~3.09(m, 2H), 3.92(s, 3H), 4.78(s, 2H), 6.26(brs, 1H), 7.04(s, 1H), 7.08~7.28(m, 7H), 7.52 (brd, J=8.4Hz, 1H) (CDCl$_3$) | 192~194 |
| 47 | 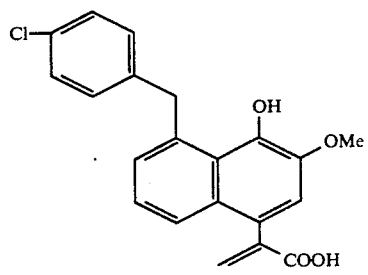<br>2-[5-(p-chlorobenzyl)-4-hydroxy-3-methoxy-1-naphthyl]-2-propenoic acid | colorless crystal | 3.84(s, 3H), 4.68(s, 2H), 5.83(s, 1H), 6.44(s, 1H), 7.04~7.28(m, 7H), 7.38 (brd, J=8.4Hz, 1H), 9.04(s, 1H), 12.66 (brs, 1H) (DMSO-d$_6$) | above 200 (dec.) |
| 48 | 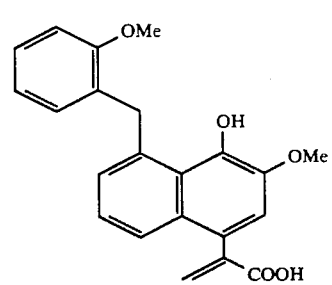<br>2-[4-hydroxy-5-(o-methoxybenzyl)-3-methoxy-1-naphthyl]-2-propenoic acid | yellow crystal | 3.86(s, 3H), 3.94(s, 3H), 4.72(s, 2H), 5.98(s, 1H), 6.28(brs, 1H), 6.74~6.84 (m, 3H), 6.90(brd, J=8.2Hz, 1H), 7.05 (brd, J=8.2Hz, 1H), 7.10~7.26(m, 3H), 7.54(brd, J=8.3Hz, 1H) (CDCl$_3$) | 195~198 |
| 49 | 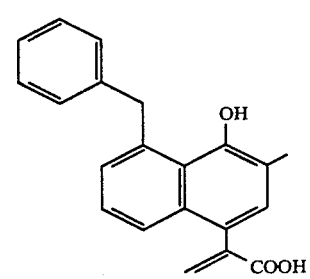<br>2-(5-benzyl-4-hydroxy-3-methyl-1-naphthyl)-2-propenoic acid | pale-yellow crystal | 2.26(s, 3H), 4.75(s, 2H), 5.76(s, 1H), 6.42(s, 1H), 7.00~7.42(m, 9H), 8.77(s, 1H), 12.62(brs, 1H) (DMSO-d$_6$) | 167~169 |

TABLE 3-continued

| Ex. No. | Objective compound structural formula and name | form | $^1$H-NMR (400 MHz) δ, MS m/z | m.p. (°C.) |
|---|---|---|---|---|
| 50 | 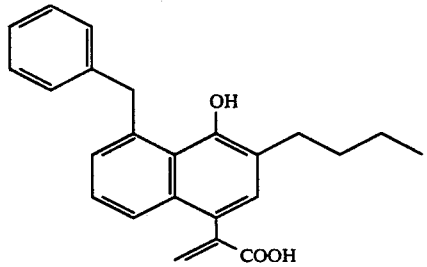<br>2-(5-benzyl-3-butyll-4-hydroxy-1-naphthyl)-2-propenoic acid | yellow crystal | 0.88 (t, J=7.2Hz, 3H), 1.24~1.37(m, 2H), 1.40~1.54(m, 2H), 2.66(t, J=7.2Hz, 2H), 4.76(s, 3H), 5.78(s, 1H), 6.42(s, 1H), 6.98~7.40(m, 9H), 8.72(s, 1H), 12.62 (brs, 1H)<br>(DMSO-d$_6$) | 167~170 |
| 51 | 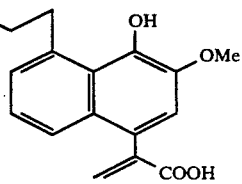<br>2-(4-hydroxy-3-methoxy-5-pentyl-1-naphthyl)-2-propenoic acid | yellow crystal | 0.90(t, J=7.3Hz, 3H), 1.30~1.44(m, 4H), 1.63~1.76(m, 2H), 3.28(t, J=7.3Hz, 2H), 3.98(s, 3H), 5.95(s, 1H), 6.40(brs, 1H), 6.76(s, 1H), 7.12(s, 1H), 7.14~7.26(m, 2H), 7.48(brd, J=8.3Hz, 1H)<br>(CDCl$_3$) | 158~159 |
| 52 | 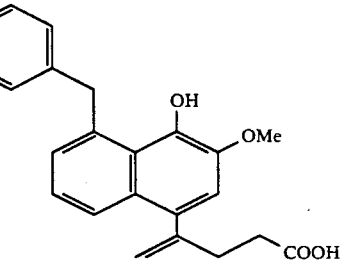<br>4-(5-benzyl-4-hydroxy-3-methoxy-1-naphthyl)-4-pentenoic acid | colorless crystal | 2.48(t, J=7.0Hz, 2H), 2.82(t, J=7.0Hz, 2H), 3.94(s, 3H), 4.78(s, 2H), 5.12(s, 1H), 5.42(s, 1H), 6.24(brs, 1H), 7.04(s, 1H), 7.10~7.27(m, 7H), 7.76(brd, J=8.4Hz, 1H)<br>(CDCl$_3$) | 137~138 |

EXAMPLE 53

2-(5-Benzyl-4-hydroxy-3-isopropyl-1-naphthyl)-3-methyl-2-butenoic acid

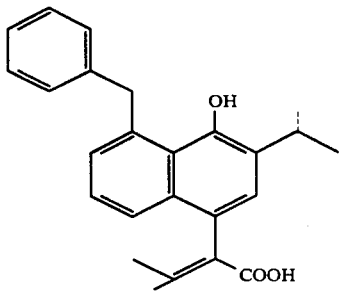

(a) synthesis of 2-(5-benzyl-4-methoxy-1-naphthyl)-3-methyl-2-butenoic acid

-continued

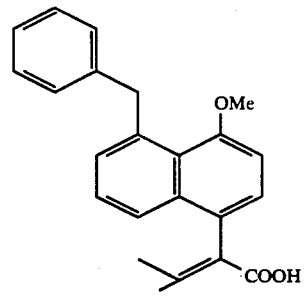

26 g of the ester prepared in the Referential Example 22 was dissolved in ethanol/water (300 ml/50 ml), followed by the addition of 6 g of sodium hydroxide. The obtained mixture was stirred under heating for 30 minutes, followed by the addition of 300 ml of 1N hydrochloric acid. The obtained mixture was extracted with ethyl acetate. The organic layer was washed with a saturated aqueous solution of sodium chloride, dried over anhydrous magnesium sulfate and distilled in a vacuum to remove the solvent. The residue was dissolved in 250 ml of tetrahydrofuran to give a solution. 188 ml of a 2M solution of isopropylmagnesium chloride in tetrahydrofuran was dropped into the solution under cooling with ice. After the completion of the dropping, the obtained mixture was stirred under cooling with ice for one hour, followed by the addition of 300 ml of a saturated aqueous solution of ammonium chloride. The obtained mixture was extracted with ethyl acetate. The organic layer was washed with a saturated aqueous solution of sodium chloride, dried over anhydrous magnesium sulfate and distilled in a vacuum to remove the solvent. The residue was dissolved in 300 ml of 1,4-dioxane, followed by the addition of 5 ml of concentrated sulfuric acid. The obtained mixture was stirred under heating for one hour and cooled to room temperature, followed by the addition of 300 ml of water. The obtained mixture was extracted with ethyl acetate. The organic layer was washed with a saturated aqueous solution of sodium chloride, dried over anhydrous magnesium sulfate and distilled in a vacuum to remove the solvent. The residue was purified by silica gel column chromatography (developer: 20% ethyl acetate/hexane) to give 5.6 g of the title compound as a yellow powder.

¹H-NMR (400 MHz, CDCl₃) δ: 1.58 (s, 3H), 2.32 (s, 3H), 3.71 (s, 3H), 4.69 (s, 2H), 6.75 (d, J=8.0 Hz, 1H) 6.95~7.28 (m, 7H), 7.25 (t, J=8.0 Hz, 1H), 7.62 (d, J=8.0 Hz, 1H).

(b) synthesis of methyl 2-(5-benzyl-4-methoxy-1-naphthyl)-3-methyl-2-butenoate

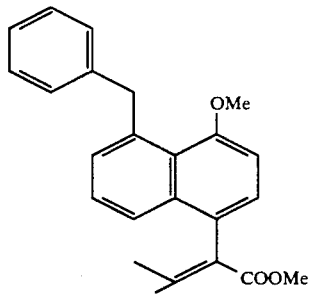

5.6 g of the carboxylic acid prepared in the step (a) was dissolved in methanol/dichloromethane (50 ml/10 ml) to give a solution. 20 ml of a 10% solution of trimethylsilyldiazomethane in dichloromethane was dropped into the solution under cooling with ice. The obtained mixture was stirred for 30 minutes and distilled in a vacuum to remove the solvent. 5.1 g of the title compound was obtained as a pale-yellow powder.

¹H-NMR (400 MHz, CDCl₃) δ: 1.55 (s, 3H), 2.29 (s, 3H), 3.58 (s, 3H), 3.72 (s, 3H), 4.71 (s, 2H), 6.95 (d, J=8.0 Hz, 1H), 7.05~7.28 (m, 7H), 7.36 (t, J=8.0 Hz, 1H), 7.66 (d, J=8.0 Hz, 1H).

(c) synthesis of methyl 2-(5-benzyl-3-formyl-4-methoxy-1-naphthyl)-3-methyl-2-butenoate -continued

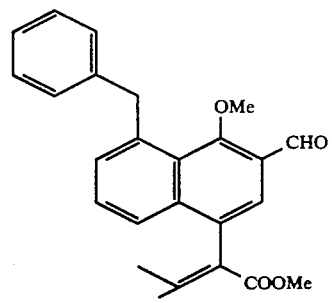

5.1 g of the methyl ester prepared in the step (b) was dissolved in 100 ml of dichloromethane to give a solution. 2.3 ml of titanium tetrachloride was added to the solution under cooling with ice, followed by the dropwise addition of 1.9 ml of dichloromethyl methyl ether. The obtained mixture was stirred under cooling with ice for 30 minutes and poured onto ice-water. The obtained mixture was extracted with dichloromethane. The organic layer was washed with a saturated aqueous solution of sodium chloride, dried over anhydrous magnesium sulfate and distilled in a vacuum to remove the solvent. The residue was purified by silica gel column chromatography (developer: 10% ethyl acetate/hexane) to give 4.2 g of the title compound as a yellow oil.

¹H-NMR (400 MHz, CDCl₃) δ: 1.54 (s, 3H), 2.33 (s, 3H), 3.57 (s, 3H), 3.84 (s, 3H), 4.73 (s, 2H), 7.06~7.33 (m, 6H), 7.49 (t, J=8.0 Hz, 1H), 7.66 (s, 1H), 7.73 (d, J=8.0 Hz, 1H), 10.52 (s, 1H).

(d) synthesis of methyl 2-(5-benzyl-3-formyl-4-hydroxy-1-naphthyl)-3-methyl-2-butenoate

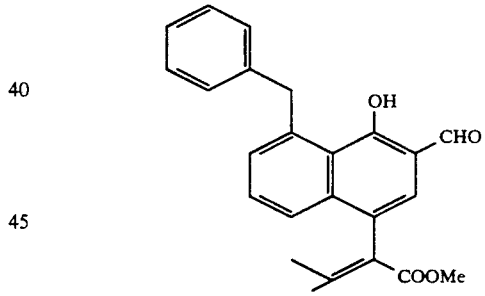

4.2 g of the formyl derivative prepared in the step (c) was dissolved in 50 ml of dichloromethane to give a solution. 11 ml of a 1M solution of boron tribromide in dichloromethane was added to the solution under cooling. The obtained mixture was stirred for 30 minutes and poured onto ice-water. The obtained mixture was extracted with dichloromethane. The organic layer was dried over anhydrous magnesium sulfate and distilled in a vacuum to remove the solvent. The residue was purified by silica gel column chromatography (developer: 6% ethyl acetate/hexane) to give 3.75 g of the title compound as a yellow powder.

¹H-NMR (400 MHz, CDCl₃) δ: 1.59 (s, 3H), 2.32 (s, 3H), 3.60 (s, 3H), 4.84 (s, 2H), 7.20 (d, J=8.0 Hz, 2H), 7.12~7.32 (m, 5H), 7.53 (t, J=8.0 Hz, 1H), 7.65 (d, J=8.0 Hz, 1H), 9.87 (s, 1H), 13.36 (s, 1H).

(e) synthesis of methyl 2-(5-benzyl-3-formyl-4-methoxymethoxy-1-naphthyl)-3-methyl-2-butenoate

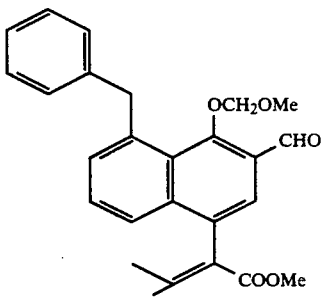

3.75 g of the phenol prepared in the step (d) was dissolved in dichloromethane, followed by the addition of 5.2 ml of diisopropylethylamine. 1.5 ml of chloromethyl methyl ether was dropped into the obtained mixture. The obtained mixture was stirred at room temperature for one hour and washed with 1% aqueous hydrochloric acid. The organic layer was dried over anhydrous magnesium sulfate and distilled in a vacuum to remove the solvent. 4.19 g of the title compound was obtained as a crude product.

(f) synthesis of methyl 2-[5-benzyl-3-(1-hydroxyethyl)-4-methoxymethoxy-1-naphthyl]-3-methyl-2-butenoate

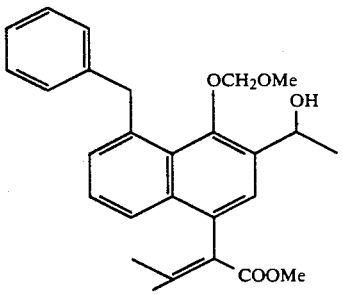

4.19 g of the methoxymethyl ether prepared in the step (e) was dissolved in 40 ml of tetrahydrofuran. The obtained solution was cooled to −70° C., followed by the dropwise addition of 8 ml of a 1.5M solution of methyllithium in ether. The obtained mixture was stirred at −70° C. for 20 minutes, followed by the addition of a saturated aqueous solution of ammonium chloride. The obtained mixture was extracted with ethyl acetate. The organic layer was dried over anhydrous magnesium sulfate and distilled in a vacuum to remove the solvent. The residue was purified by silica gel column chromatography (developer: 20% ethyl acetate/hexane) to give 3.35 g of the title compound as a pale-yellow oil.

$^1$H-NMR (400 MHz, CDCl$_3$) δ: 1.45~1.62 (m, 3H), 1.54 (s, 3H), 2.31 (s, 3H), 3.54 (s, 3H), 3.58 (s, 3H), 4.64 (d, J=16 Hz, 1H), 4.73 (d, J=16 Hz, 1H), 4.70~4.87 (m, 2H), 5.38~5.52 (m, 1H), 7.07~7.45 (m, 8H), 7.67 (d, J=8.0 Hz, 1H).

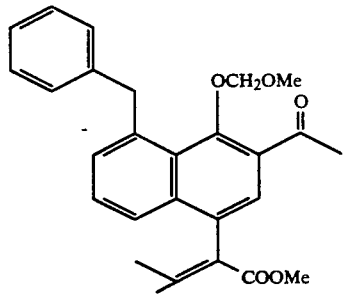

3.35 g of the alcohol prepared in the step (f) was dissolved in 200 ml of dichloromethane, followed by the addition of 25 g of manganese dioxide. The obtained mixture was heated under reflux for 2 hours, cooled to room temperature and filtered through Celite. THe filtrate was distilled in a vacuum to remove the solvent. 3.33 g of the title compound was obtained as a yellow oil in a crude state.

$^1$H-NMR (400 MHz, CDCl$_3$) δ: 1.54 (s, 3H), 2.32 (s, 3H), 2.64 (s, 3H), 3.32 (s, 3H), 3.58 (s, 3H), 4.73 (d, J=16 Hz, 1H), 4.79 (d, J=16 Hz, 1H), 4.80 (d, J=12 Hz, 1H), 4.83 (d, J=12 Hz, 1H), 7.10~7.33 (m, 6H), 7.37 (s, 1H), 7.41 (t, J=8.0 Hz, 1H), 7.70 (d, J=8.0 Hz, 1H).

(h) synthesis of methyl 2-(5-benzyl-3-isopropenyl-4-methoxymethoxy-1-naphthyl)-3-methyl-2-butenoate

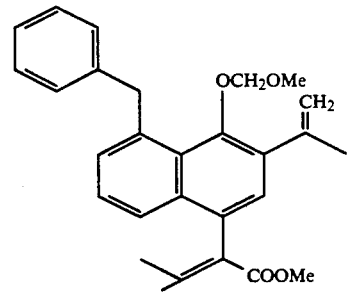

3 g of the acetyl derivative prepared in the step (g) was dissovled in 40 ml of dimethoxyethane, followed by the addition of 3 g of methyltriphenylphosphonium bromide and 0.4 g of sodium hydride (55% suspension in oil). The obtained mixture was stirred under heating for one hour, cooled to room temperature and poured onto ice-water. The obtained mixture was extracted with ethyl acetate. The organic layer was dried over anhydrous magnesium sulfate and distilled in a vacuum to remove the solvent. The residue was purified by silica gel column chromatography (developer: 10% ethyl acetate/hexane) to give 1.65 g of the title compound as a yellow oil.

$^1$H-NMR (400 MHz, CDCl$_3$) δ: 1.54 (s, 3H), 2.19 (s, 3H), 2.28 (s, 3H), 3.43 (s, 3H), 3.59 (s, 3H), 4.81 (s, 2H), 4.79 (s, 2H), 5.17 (d, J=1.8 Hz, 1H), 5.25 (d, J=1.8 Hz, 1H), 7.10~7.32 (m, 8H), 7.63 (d, J=8.0 Hz, 1H).

(g) synthesis of methyl 2-(3-acetyl-5-benzyl-4-methoxymethoxy-1-naphthyl)-3-methyl-2-butenoate (i) synthesis of methyl 2-(5-benzyl-3-isopropyl-4-methoxymethoxy-1-naphthyl)-3-methyl-2-butenoate

75

-continued

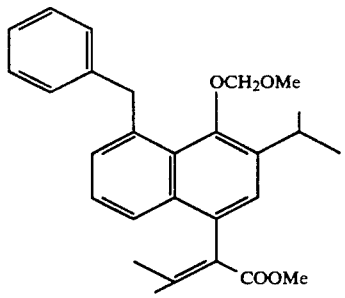

1.1 g of the isopropenyl derivative prepared in the step (h) was dissolved in methanol/tetrahydrofuran (30 ml/10 ml), followed by the addition of 0.5 g of 10% Pd-C (containing 50% of water). The obtained mixture was stirred at room temperature in an atmosphere of hydrogen for 5 hours and filtered through Celite. The filtrate was distilled in a vacuum to give 1.1 g of the title compound in a crude state as a yellow oil.

$^1$H-NMR (400 MHz, CDCl$_3$) δ: 1.26 (d, J=7.2 Hz, 3H), 1.28 (d, J=7.2 Hz, 3H), 1.52 (s, 3H), 2.28 (s, 3H), 3.53 (s, 3H), 3.59 (s, 3H), 3.60~3.68 (m, 1H), 4.77 (s, 2H), 4.87 (s, 2H), 7.08 (d, J=8.0 Hz, 1H), 7.10~7.32 (m, 7H), 7.62 (d, J=8.0 Hz, 1H).

(j) synthesis of 2-(5-benzyl-4-hydroxy-3-isopropyl-1-naphthyl)-3-methyl-2-butenoic acid

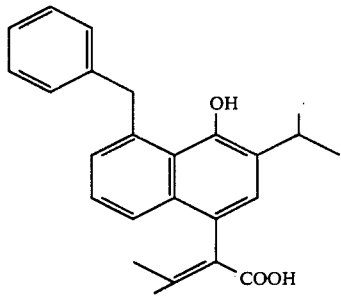

1.1 g of the isopropyl derivative prepared in the step (i) was dissolved in methanol/water (20 ml/2 ml), followed by the addition of 1 g of sodium hydroxide. The obtained mixture was heated under reflux for 4 hours and cooled to room temperature, followed by the addition of 30 ml of 1N aqueous hydrochloric acid. The obtained mixture was extracted with ethyl acetate. The organic layer was dried over anhydrous magnesium sulfate and distilled in a vacuum to remove the solvent. The obtained residue was dissolved in 20 ml of acetone, followed by the addition of 10 ml of concentrated hydrochloric acid. The obtained mixture was stirred at room temperature for 30 minutes to precipitate a crystal. This crystal was recovered by filtration and washed with water sufficiently to give 0.7 g of the title compound as a pale-yellow crystal.

m.p.: 264° to 266° C.

$^1$H-NMR (400 MHz, CDCl$_3$) δ: 1.25 (d, J=7.0 Hz, 3H), 1.27 (d, J=7.0 Hz, 3H), 1.57 (s, 3H), 2.34 (s, 3H), 3.14~3.27 (m, 1H), 4.73 (d, J=20 Hz, 1H), 4.77 (d, J=20 Hz, 1H), 7.15 (s, 1H), 7.16~7.35 (m, 8H), 7.66 (d, J=8.0 Hz, 1H).

MS m/z (Pos, FAB): 374 (M+).

76

EXAMPLE 54

2-(3-Acetyl-5-benzyl-4-hydroxy-1-naphthyl)-3-methyl-2-butenoic acid

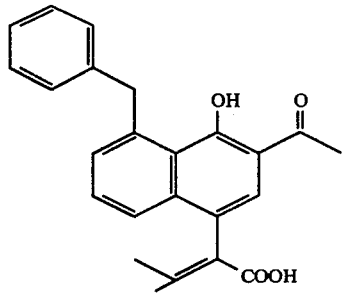

The title compound was prepared from the 2-acetyl derivative prepared in the step (g) of the Example 53 in a similar manner to that of the step (b) of the Example 40.

m.p.: 241.0° C. (dec.).

$^1$H-NMR (400 MHz, CDCl$_3$) δ: 1.60 (s, 3H), 2.35 (s, 3H), 2.62 (s, 3H), 4.82 (s, 2H), 7.11~7.28 (m, 6H), 7.40 (s, 1H), 7.46 (br t, J=8.3 Hz, 1H), 7.56 (br d, J=8.3 Hz, 1H), 14.76 (s, 1H).

EXAMPLE 55

2-(5-Benzyl-4-hydroxy-3-methoxy-1-maphthyl)-3, 3-dichloro-2-propenoic acid

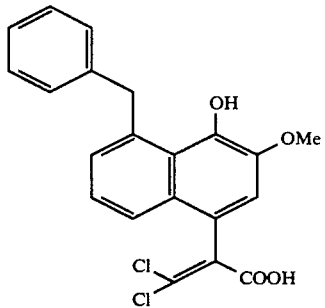

(a) synthesis of ethyl 2-(5-benzyl-3-methoxy-4-methoxymethoxy-1-naphthyl)-3, 3-dichloro-2-propenoate

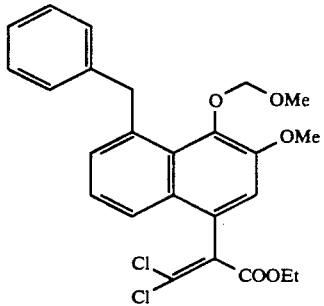

8.37 g of triphenylphosphine and 3.23 g of the keto-ester prepared in the Referential Example 12 were dissolved in 20 ml of acetonitrile, followed by the addition of 3.2 ml of carbon tetrachloride in a stream of nitrogen. The obtained mixture was stirred at room temperature in a stream of nitrogen for 4 hours and poured into ether/water (120 ml/40 ml). The organic layer wad washed with water, dried over anhydrous magnesium sulfate and distilled in a vacuum to remove the solvent.

The residue was purified by silica gel column chromatography (developer: 10% ethyl acetate/hexane) to give 3.3 g of the title compound as a yellow oil.

¹H-NMR (400 MHz, CDCl₃) δ: 1.13 (t, J=7 Hz, 3H), 3.47 (s, 3H), 3.93 (s, 3H), 4.22 (q, J=7 Hz, 2H), 4.70 (br d, J=13 Hz, 1H), 4.80 (br d, J=13 Hz, 1H), 5.11 (s, 2H), 7.10~7.30 (m, 8H), 7.70 (d, J=7 Hz, 1H).

(b) synthesis of 2-(5-benzyl-3-methoxy-4-methoxy methoxy-1-naphthyl)-3, 3-dichloro-2-propenoic acid

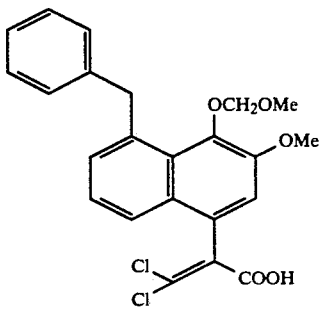

2.55 g of the dichloro derivative prepared in the step (a) and 0.74 ml of 8N potassium hydroxide were added to a dimethyl sulfoxide (55 ml) -water (10 ml) mixture. The obtained mixture was stirred at room temperature for one hour, followed by the addition of water. The obtained mixture was acidified with 6N hydrochloric acid and extracted with ether. The organic layer was washed with a saturated aqueous solution of sodium chloride, dried over anhydrous magnesium sulfate and concentrated in a vacuum. The obtained residue was purified by silica gel column chromatography (developer: 5% methanol/dichloromethane) to give 2.36 g of the title compound as a yellow oil.

¹H-NMR (400 MHz, CDCl₃) δ: 3.46 (s, 3H), 3.86 (s, 3H), 4.74 (br d, J=14 Hz, 1H), 4.84 (br d, J=14 Hz, 1H), 5.09 (s, 2H), 7.1~7.25 (m, 8H), 7.71 (d, J=8 Hz, 1H).

(c) 2-(5-Benzyl-4-hydroxy-3-methoxy-1-naphthyl)-3, 3-dichloro-2-propenoic acid

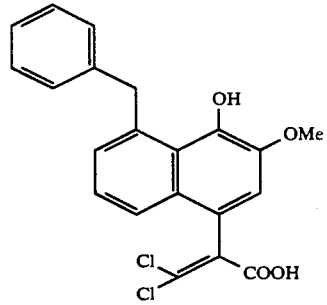

2.55 g of the carboxylic acid prepared in the step (b) was dissolved in 150 ml of 1,4-dioxane, followed by the addition 1.25 ml of water and 1.25 ml of concentrated sulfuric acid in this order. The obtained mixture was stirred at room temperature for 2 hours, followed by the addition of water. The obtained mixture was extracted with ether. The ethereal layer was washed with water, dried over anhydrous magnesium sulfate and distilled in a vacuum to remove the solvent. The residue was purified by silica gel column chromatography (developer: 5% methanol/dichloromethane) to give 2.0 g of the title compound as a yellow crystal.

m.p.: 152° to 154° C.

¹H-NMR (400 MHz, CDCl₃) δ: 3.71 (s, 3H), 4.70 (br d, J=14 Hz, 1H), 4.80 (br d, J=14 Hz, 1H), 6.30 (br s, 1H), 7.11 (s, 1H), 7.1~7.25 (m, 7H), 7.59 (d, J=8 Hz, 1H).

MS m/z (Pos, FAB): 402 (M⁺).

EXAMPLE 56 syn- and anti-2-(5-Benzyl-4-hydroxy-3-methoxy-1-naphthyl)-2-methoxyiminoacetic acid

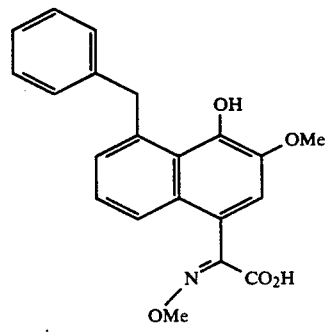
syn-isomer

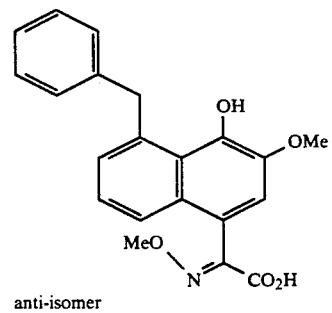
anti-isomer (a) synthesis of ethyl 2-(5-benzyl-3-methoxy-4-methoxymethoxy-1-naphthyl)-2-methoxy-iminoacetate

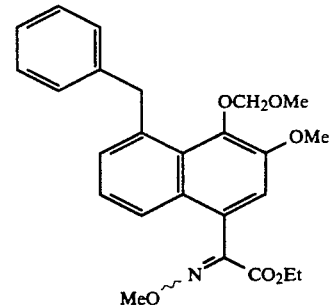

Ethanol-water (50 ml-10 ml), 1.41 g of O-methylhydroxylamine and 2.10 g of potassium hydroxide were added to 2.38 g of the ketoester prepared in the Referential Example 12. The obtained mixture was heated under reflux for 45 minutes. After the completion of the reaction, the reaction mixture was poured into water. The obtained mixture was extracted with ethyl acetate. The organic layer was dried over anhydrous sodium sulfate and distilled in a vacuum to remove the solvent. 1.45 g of the title compound was obtained.

(b) synthesis of syn- and anti-2-(5-benzyl-3-methoxy-4-methoxymethoxy-1-naphthyl -continued
2-methoxyiminoacetic acid

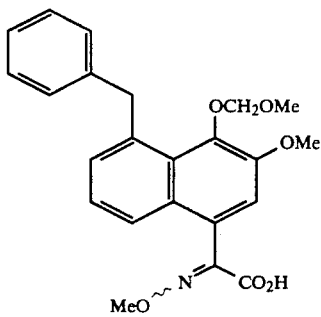

1.45 g of the methoxyimino derivative prepared in the step (a) was dissolved in methanol/water (15 ml/3 ml), followed by the addition of 0.8 ml of 8N sodium hydroxide. The obtained mixture was stirred at room temperature. After the completion of the reaction, ice was added to the reaction mixture and the pH of the resulting mixture was adjusted to 4 to 5 by the addition of 1N hydrochloric acid. The resulting mixture was extracted with ethyl acetate under salting out. The organic layer was dried over anhydrous sodium sulfate and distilled in a vacuum to remove the solvent. The residue was purified by silica gel column chromatography (developer: 0 to 4% methanol/dichloromethane) to give 0.69 g of the syn isomer and 0.51 g of the anti-isomer each as a reddish brown oil. anti-isomer $^1$H-NMR (400 MHz, CDCl$_3$-CD$_3$OD) δ: 3.45 (s, 3H), 3.88 (s, 3H), 3.98 (s, 3H), 4.76 (s, 2H), 5.04 (s, 2H), 7.0∼7.3 (m, 7H), 7.5 (s, 1H), 8.25 (d, J=7 Hz, 1H).

syn-isomer $^1$H-NMR (400 MHz, CDCl$_3$) δ: 3.48 (s, 3H), 3.90 (s, 3H), 4.05 (s, 3H), 4.8 (s, 2H), 5.1 (s, 2H), 7.0∼7.3 (m, 10H).

(c) synthesis of syn-2-(5-benzyl-4-hydroxy-3-methoxy-1-naphthyl)-2-methoxyiminoacetic acid

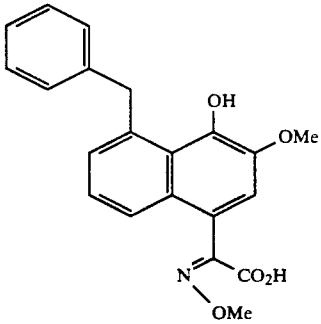

0.69 g of the syn-carboxylic acid prepared in the step (b) was dissolved in 5 ml of acetone, followed by the addition of 1 ml of 6N hydrochloric acid. The obtained mixture was stirred at room temperature to complete a reaction. The reaction mixture was poured into water and the obtained mixture was extracted with ethyl acetate. The organic layer was dried over anhydrous sodium sulfate and distilled in a vacuum to remove the solvent. The residue was recrystallized from hexane/diethyl ether to give 0.40 g of the title compound as a pale-yellow crystal.

m.p.: 133° to 134° C.

$^1$H-NMR (400 MHz, DMSO-d$_6$) δ: 3.82 (s, 3H), 3.84 (s, 3H), 4.7 (s, 2H), 7.0∼7.25 (m, 10H), 9.23 (s, 1H).

MS m/z (Pos, FAB): 365 (M+).

(d) synthesis of anti-2-(5-benzyl-4-hydroxy-3-methoxy-1-naphthyl)-2-methyliminoacetic acid

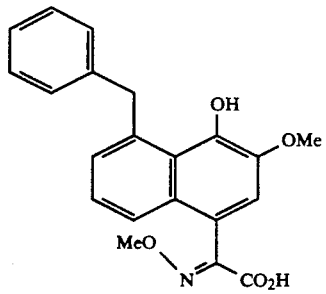

0.50 g of the anti-carboxylic acid prepared in the step (b) was suspended in 10 ml of dichloroethane, followed by the addition of 1.0 ml of trifluoroacetic acid. The obtained mixture was stirred at room temperature to complete a reaction. The reaction mixture was distilled in a vacuum to remove the solvent. The residue was recrystallized from hexane/diethyl ether to give 0.35 g of the title compound as a pale-yellow crystal.

m.p.: 150° C. (dec.).

$^1$H-NMR (400 MHz, DMSO-d$_6$) δ: 3.78 (s, 3H), 3.82 (s, 3H), 4.7 (s, 2H), 7.0∼7.23 (m, 8H), 7.3 (d, J=7 Hz, 1H), 9.1 (br s, 1H).

MS m/z (Pos, FAB): 365 (M+).

EXAMPLE 57

(Z)-2-(4-Acetyloxy-5-benzyl-3-methoxy-1-naphthyl)-2-pentenoic acid

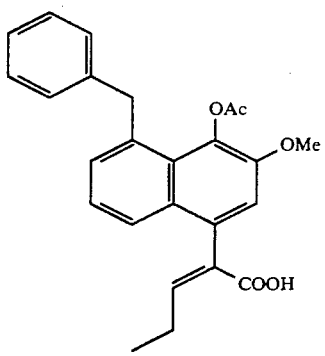

(a) synthesis of methoxymethyl (Z)-2-(5-benzyl-4-hydroxyl-3-methoxy-1-naphthyl)-2-pentenoate

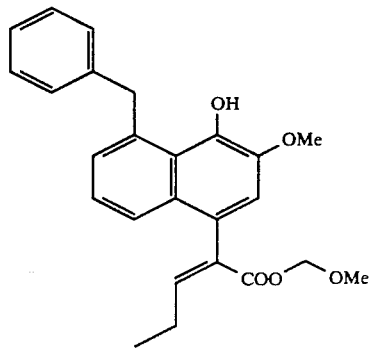

30 ml of dichloromethane and 1.6 ml of N,N-diisopropylethylamine were added to 2.21 g of the α,β-unsaturated carboxylic acid prepared in the Example 2, followed by the addition of 0.69 ml of chloromethyl ether under cooling with ice. The obtained mixture was stirred for 25 minutes under cooling with ice, washed with 1% aqueous hydrochloric acid once and with water once, dried over anhydrous sodium sulfate and filtered. The filtrate was distilled to remove the solvent. The obtained residue was subjected to silica gel column chromatography to give 2.26 g of the title compound.

$^1$H-NMR (400 MHz, CDCl$_3$) δ: 1.19 (t, J=7.5 Hz, 3H), 2.74 (quint, J=7.5 Hz, 2H), 3.14 (s, 3H), 3.96 (s, 3H), 4.77 (br s, 2H), 5.19 (s, 2H), 6.26 (t, J=7.5 Hz, 1H), 6.27 (s, 1H), 7.12 (s, 1H), 7.1~7.3 (m, 7H), 7.64 (br d, J=8.4 Hz, 1H).

(b) synthesis of methoxymethyl (Z)-2-(4-acetyloxy-5-benzyl-3-methoxy-1-naphthyl)-2-pentenoate

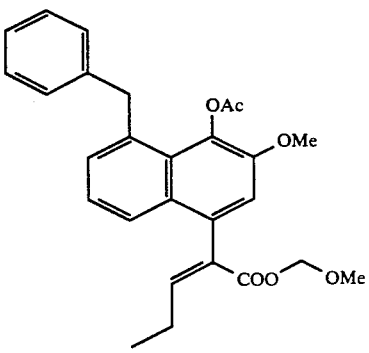

30 ml of dichloromethane and 1.08 g of N,N-diisopropylethylamine were added to 2.26 g of the methoxymethyl ester prepared in the step (a), followed by the addition of 0.59 ml of acetyl chloride under cooling with ice. The obtained mixture was stirred under cooling with ice for 20 minutes, washed with 1% aqueous hydrochloric acid and water, dried over anhydrous magnesium sulfate and filtered. The filtrate was distilled to remove the solvent. 2.56 g of the title compound was obtained as an oil.

$^1$H-NMR (400 MHz, CDCl$_3$) δ: 1.21 (t, J=7.5 Hz, 3H), 2.03 (s, 3H), 2.79 (quint, J=7.5 Hz, 2H), 3.17 (s, 3H), 3.91 (s, 3H), 4.59 (br s, 2H), 5.21 (s, 2H), 6.34 (t, J=7.5 Hz, 1H), 7.0~7.3 (m, 8H), 7.72 (d, J=8.4 Hz, 1H).

(c) synthesis of (Z)-2-(4-acetyloxy-5-benzyl-3-methoxy-1-naphthyl)-2-pentenoic acid

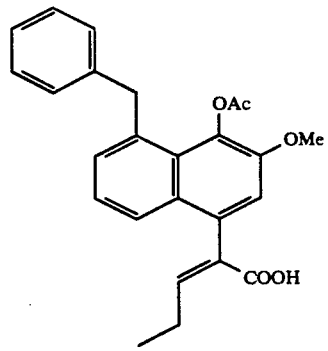

2.56 g of the acetyloxy derivative prepared in the step (b) was dissolved in 35 ml of acetone, followed by the addition of 1 ml of water and 6 ml of concentrated hydrochloric acid in this order. The obtained mixture was stirred at room temperature for 1.5 hours, followed by the addition of water. The obtained mixture was extracted with ethyl acetate. The organic layer was washed with water and a saturated aqueous solution of sodium chloride, dried over anhydrous magnesium sulfate and filtered. The filtrate was distilled to remove the solvent. Diisopropyl ether was added to the residue to precipitate a crystal. This crystal was recovered by filtration and washed with diisopropyl ether to give 2.01 g of the title compound.

m.p.: 182° to 184° C.

$^1$H-NMR (400 MHz, CDCl$_3$) δ: 1.17 (t, J=7.5 Hz, 3H), 2.01 (s, 3H), 2.78 (quint, J=7.5 Hz, 2H), 3.89 (s, 3H), 4.58 (br s, 2H), 6.39 (t, J=7.5 Hz, 1H), 7.05~7.3 (m, 8H), 7.70 (d, J=8.4 Hz, 1H).

MS m/z (Pos, FAB): 404 (M+), 362.

EXAMPLES 58 TO 61

The acetyl derivatives listed in Table 4 were each prepared from the phenolcarboxylic acid prepared in the Example 1, 3, 4 or 40 in a similar manner to that of the Example 57.

TABLE 4

| Ex. No. | Objective compound structural formula and name | form | $^1$H-NMR (400 MHz) δ, MS m/z | m.p. (°C.) |
|---|---|---|---|---|
| 58 | (Z)-2-(4-acetoxy-5-benzyl-3-methoxy-1-naphthyl)-2-butenoic acid | colorless crystal | 2.02(s, 3H), 2.31(d, J=7.0Hz, 3H), 3.88 (s, 3H), 4.58(s, 2H), 6.51(q, J=7.0Hz, 1H), 7.06(d, J=8.0Hz, 2H), 7.14(d, J=8.0Hz, 1H), 7.21(s, 1H), 7.16~7.30(m, 4H), 7.69(d, J=8.0Hz, 1H) (CDCl$_3$) (Pos, FAB): 390 (M+) | 190~192 |

TABLE 4-continued

| Ex. No. | Objective compound structural formula and name | form | $^1$H-NMR (400 MHz) δ, MS m/z | m.p. (°C.) |
|---|---|---|---|---|
| 59 | (E)-2-(4-acetoxy-5-benzyl-3-methoxy-1-naphthyl)-2-butenoic acid | pale-yellow crystal | 1.64(d, J=7.2Hz, 3H), 2.03(s, 3H), 3.87 (s, 3H), 4.58(s, 2H), 7.04~7.32(m, 8H), 7.50~7.60(m, 2H) (CDCl$_3$) | 178~180 |
| 60 | (Z)-2-(4-acetoxy-5-benzyl-3-methoxy-1-naphthyl)-2-hexenoic acid | colorless crystal | 1.02(t, J=7.3Hz, 3H), 1.59(sixtet, J=7.3Hz, 2H), 2.00(s, 3H), 2.75(dt, J=7.5Hz, 7.3Hz, 2H), 3.89(s, 3H), 4.58(s, 2H), 6.40(t, J=7.5Hz, 1H), 7.00~7.30(m, 8H), 7.70(dd, J=8.4Hz, 1.1Hz, 1H) (CDCl$_3$) (Pos, FAB): 418 (M$^+$) | 198~200 |
| 61 | (Z)-2-(4-acetoxy-5-benzyl-3-methoxy-1-naphthyl)-4-methyl-2-pentenoic acid | pale-yellow crystal | 1.14(d, J=6.6Hz, 6H), 2.00(s, 3H), 3.50~3.60(m, 1H), 3.90(s, 3H), 4.56(brs, 1H), 6.18(d, J=10.0Hz, 1H), 7.04~7.30(m, 8H), 7.70(brd, J=8.4Hz, 1H) (CDCl$_3$) | 208~210 |

EXAMPLE 62

N,N-Diethyl-(Z)-2-(5-benzyl-4-hydroxy-3-methoxy-1-naphthyl)-2-butenamide

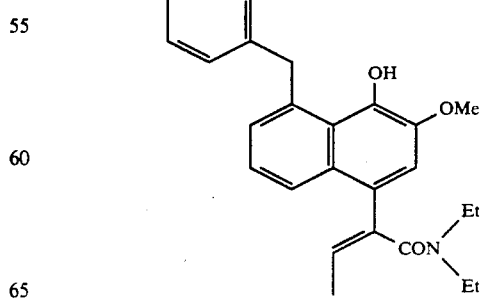

1 g of the carboxylic acid prepared in the Example 1 was dissolved in 20 ml of tetrahydrofuran to give a solution. 0.44 ml of triethylamine and 0.45 g of diethyl chlorophosphate were added to the solution under cooling with ice. The obtained mixture was stirred for 20 minutes, followed by the addition of 0.33 ml of diethylamine under cooling with ice. The obtained mixture was stirred for 30 minutes, followed by the addition of 50 ml of ethyl acetate. The obtained mixture was washed with water twice. The organic layer was dried over anhydrous magnesium sulfate and distilled in a vacuum to remove the solvent. The residue was purified by silica gel column chromatography (developer: 20 to 40% ethyl acetate/hexane) to give a yellow oil. 2 ml of diisopropyl ether was added to the oil to precipitate a crystal. This crystal was recovered by filtration to give 0.16 g of the title compound as a pale-yellow crystal.

m.p.: 86° to 87° C.

$^1$H-NMR (400 MHz, CDCl$_3$) δ: 1.01 (t, J=6.8 Hz, 3H), 1.02 (t, J=6.8 Hz, 3H), 2.36 (d, J=7.2 Hz, 3H), 3.75~3.87 (m, 4H), 3.76 (s, 3H), 4.76 (s, 2H), 6.30 (s, 1H), 6.62 (q, J=6.8 Hz, 0.5H), 6.63 (q, J=6.8 Hz, 0.5H), 7.10 (s, 1H), 7.10~7.30 (m, 7H), 7.58 (dd, J=8.4 Hz, 0.8 Hz, 1H).

MS m/z (Pos, FAB): 403 (M+).

We claim:

1. A compound of the formula:

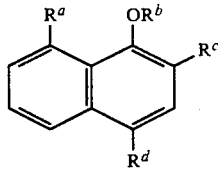

wherein R$^a$ is a benzyl group;
R$^b$ is a hydrogen atom or a lower alkyl group;
R$^c$ is a lower alkyl group; and
R$^d$ is a hydrogen atom or a group of the formula:

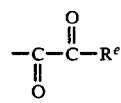

wherein R$^e$ is a hydroxyl group or a lower alkyl group.

2. A compound of the formula:

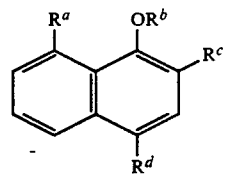

wherein R$^a$ is a benzyl group;
R$^b$ is a hydrogen atom or a lower alkyl group;
R$^c$ is a hydrogen atom or a lower alkyl group; and
R$^d$ is a group of the formula:

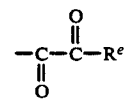

wherein R$^e$ is a hydroxyl group or a lower alkyl group.

3. A compound of the formula:

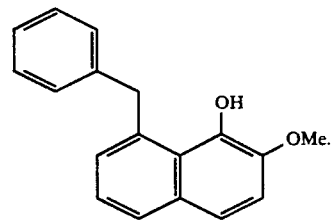

4. A compound of the formula:

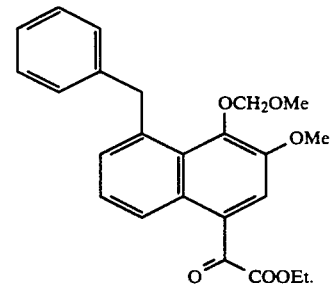

5. A compound of the formula:

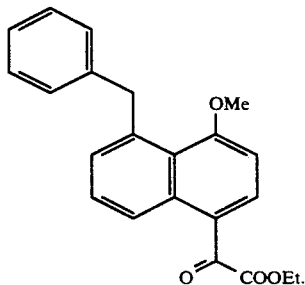

* * * * *